(12) United States Patent
Doubler et al.

(10) Patent No.: US 7,678,136 B2
(45) Date of Patent: *Mar. 16, 2010

(54) SPINAL FIXATION ASSEMBLY

(75) Inventors: Robert L. Doubler, Ida, MI (US); John E. Hammill, Sr., Rossford, OH (US)

(73) Assignee: Spinal, LLC, Palm Beach Gardens, FL (US)

( * ) Notice: Subject to any disclaimer, the term of this patent is extended or adjusted under 35 U.S.C. 154(b) by 1506 days.

This patent is subject to a terminal disclaimer.

(21) Appl. No.: 10/912,532

(22) Filed: Aug. 5, 2004

(65) Prior Publication Data

US 2005/0137594 A1 Jun. 23, 2005

Related U.S. Application Data

(63) Continuation-in-part of application No. 10/358,427, filed on Feb. 4, 2003, now Pat. No. 7,105,029, application No. 10/912,532, which is a continuation-in-part of application No. 10/618,689, filed on Jul. 9, 2003, and a continuation-in-part of application No. 10/661,371, filed on Sep. 10, 2003, and a continuation-in-part of application No. 10/673,680, filed on Sep. 26, 2003, now Pat. No. 7,335,201, and a continuation-in-part of application No. 10/733,160, filed on Dec. 10, 2003, now Pat. No. 7,118,303.

(60) Provisional application No. 60/354,408, filed on Feb. 4, 2002.

(51) Int. Cl.
*A61B 17/70* (2006.01)

(52) U.S. Cl. .................................................. 606/246

(58) Field of Classification Search .................. 606/61, 606/300, 301, 303, 305, 306, 308, 319, 86 A
See application file for complete search history.

(56) References Cited

U.S. PATENT DOCUMENTS

| | | | |
|---|---|---|---|
| 1,523,045 A * | 1/1925 | Whiteman | 411/157 |
| 4,653,969 A | 3/1987 | Summerlin et al. | |
| 4,684,284 A | 8/1987 | Bradley, Jr. | |
| 4,822,223 A | 4/1989 | Williams | |
| 5,110,244 A | 5/1992 | Garman | |
| 5,613,968 A | 3/1997 | Lin | |
| 5,628,740 A * | 5/1997 | Mullane | 606/61 |
| 5,749,690 A | 5/1998 | Kutz | |
| 5,816,761 A | 10/1998 | Cassatt | |
| 6,050,997 A * | 4/2000 | Mullane | 606/61 |
| 6,179,512 B1 | 1/2001 | Gibson et al. | |
| 6,254,602 B1 | 7/2001 | Justis | |

(Continued)

FOREIGN PATENT DOCUMENTS

DE 197 20 782 A 1 11/1998

(Continued)

*Primary Examiner*—Eduardo C Robert
*Assistant Examiner*—David Comstock
(74) *Attorney, Agent, or Firm*—McHale & Slavin, P.A.

(57) ABSTRACT

This disclosure relates to spinal fixation assemblies for use in spinal fixation constructs. The final fixation assemblies include fastening arrangements for clamping components of the assemblies at desired positions. The fastening arrangements are moved from pre-finally clamped orientations to finally clamped orientations through the use of linear force. An installation tool can be used to inhibit linear force from being transferred to the patient.

3 Claims, 19 Drawing Sheets

U.S. PATENT DOCUMENTS

| | | |
|---|---|---|
| 6,537,005 B1 | 3/2003 | Denham |
| 6,623,485 B2 * | 9/2003 | Doubler et al. ............... 606/61 |
| 7,105,029 B2 * | 9/2006 | Doubler et al. .......... 623/22.42 |
| 7,335,201 B2 * | 2/2008 | Doubler et al. ............. 606/264 |
| 2002/0114680 A1 | 8/2002 | Stoewer |
| 2003/0073996 A1 | 4/2003 | Doubler et al. |
| 2003/0149487 A1 | 8/2003 | Doubler et al. |
| 2004/0006342 A1 | 1/2004 | Altarac et al. |

FOREIGN PATENT DOCUMENTS

| | | |
|---|---|---|
| DE | 100 05 386 A 1 | 8/2001 |

* cited by examiner

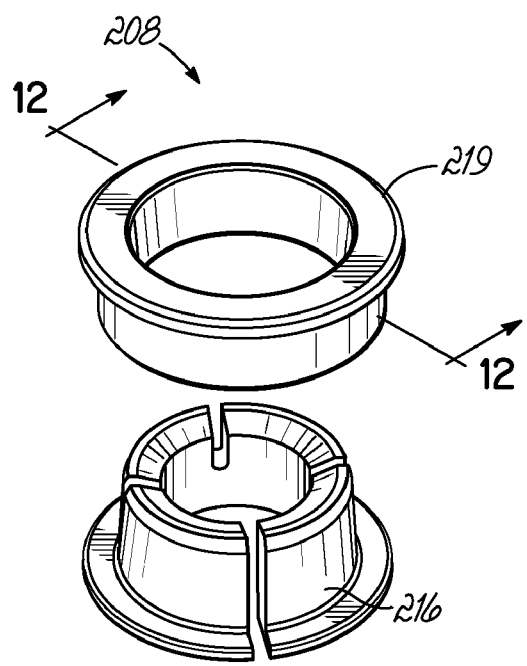
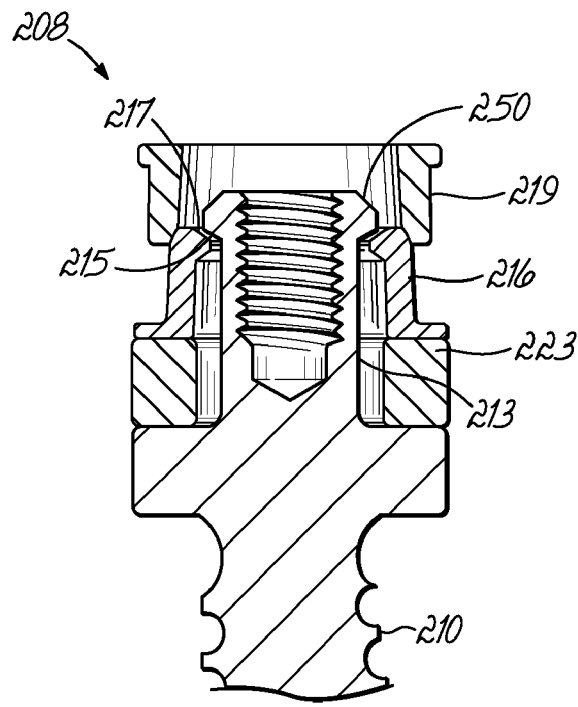
FIG. 12
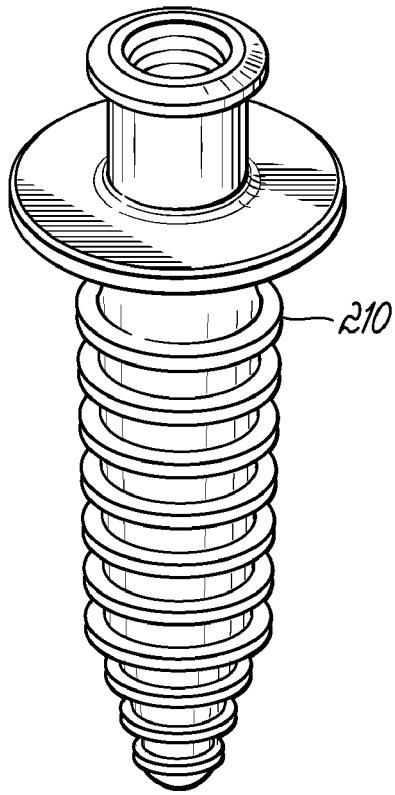
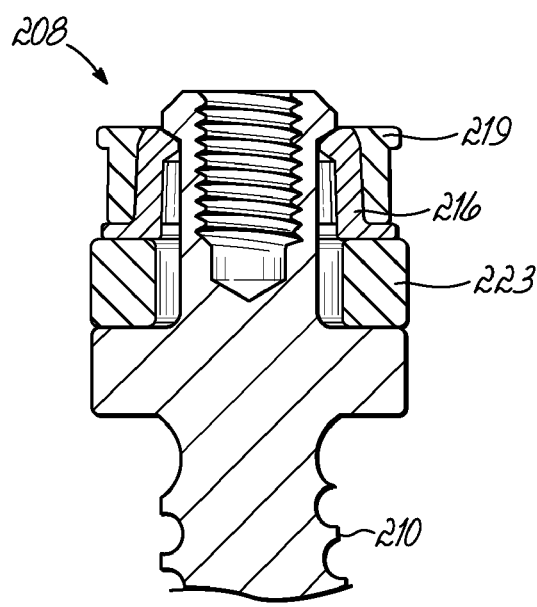
FIG. 11
FIG. 13

SPINAL FIXATION ASSEMBLY

CROSS REFERENCE TO RELATED APPLICATIONS

This application is a continuation-in-part of U.S. patent application Ser. No. 10/358,427 filed Feb. 4, 2003, now U.S. Pat. No. 7,105,029 which is hereby incorporated herein by reference in its entirety and which claims priority to provisional application Ser. No. 60/354,408 filed on Feb. 4, 2002. This application is also a continuation-in-part of U.S. patent application Ser. No. 10/618,689 filed Jul. 9, 2003, which is hereby incorporated herein by reference in its entirety. This application is further a continuation-in-part of U.S. patent application Ser. No. 10/661,371 filed Sep. 10, 2003, which is hereby incorporated herein by reference in its entirety. This application is further a continuation-in-part of U.S. patent application Ser. No. 10/673,680 filed Sep. 26, 2003, now U.S. Pat. No. 7,335,201 which is hereby incorporated herein by reference in its entirety. This application is further a continuation-in-part of U.S. patent application Ser. No. 10/733,160 filed Dec. 10, 2003, now U.S. Pat. No. 7,118,303 which is hereby incorporated herein by reference in its entirety.

TECHNICAL FIELD

The principles disclosed herein relate to bone stabilization systems. More specifically, the disclosure relates to intervertebral connection systems suited for stabilization of the spine.

BACKGROUND

Chronic back problems cause pain and disability for a large segment of the population. In many cases, the chronic back problems are caused by intervertebral disc disease and deterioration and loss of stability of the intervertebral joint. Examples of these spinal conditions include degenerative disc disease, scoliosis, spondylolithesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050 B1; 6,371,957 B1 ;6,050,997; 5,879,350; 5,725,527; 5,628,740; 5,545,165, the entire disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

In many known stabilization systems, threaded nuts are used to secure the rods to the connectors. The rods can be provisionally held in position by loosely tightening the nuts on the connectors. After desired adjustments are made with respect to the relative positioning of the bones desired to be stabilized, the nuts can be further tightened to finally secure the connector/rod construct. Typically, a torque wrench or similar device is used to achieve the required torques to finally secure the connector/rod construct. To prevent torque from being transferred to the patient while tightening the nut, an anti-torque device is frequently used in combination with the torque wrench. The effective use of the torque wrench and anti-torque device can be difficult and often is dependent upon the strength and experience of the surgeon. What are needed are alternative spine stabilization fastening techniques that do not require the use torque.

SUMMARY

One inventive aspect of the disclosure relates to spine stabilization techniques and systems that do not require torque for final tightening.

A variety of additional inventive aspects will be set forth in the description that follows. The inventive aspects can relate to individual features and combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

FIG. 11 is an exploded, perspective view illustrating a third embodiment of a spinal fixation assembly having features that are examples of inventive aspects in accordance with the principles of the present disclosure;

FIG. 12 is a cross-sectional view of the spinal fixation assembly of FIG. 11 showing the assembly in a non-finally clamped orientation;

FIG. 13 is a cross-sectional view of the spinal fixation assembly of FIG. 11 showing the assembly in a finally clamped orientation;

DETAILED DESCRIPTION

Figure 1:
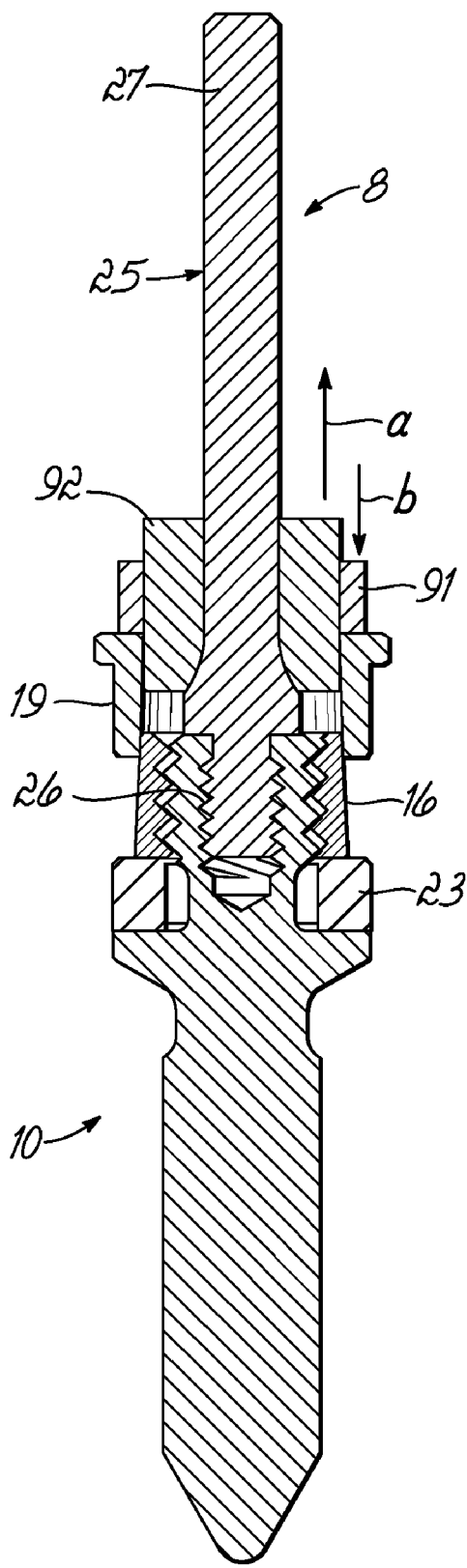
FIG. 1 is a cross-sectional view illustrating a spinal fixation assembly having features that are examples of inventive aspects in accordance with the principles of the present disclosure, the assembly is shown in a non-finally clamped orientation.
Figure 2:
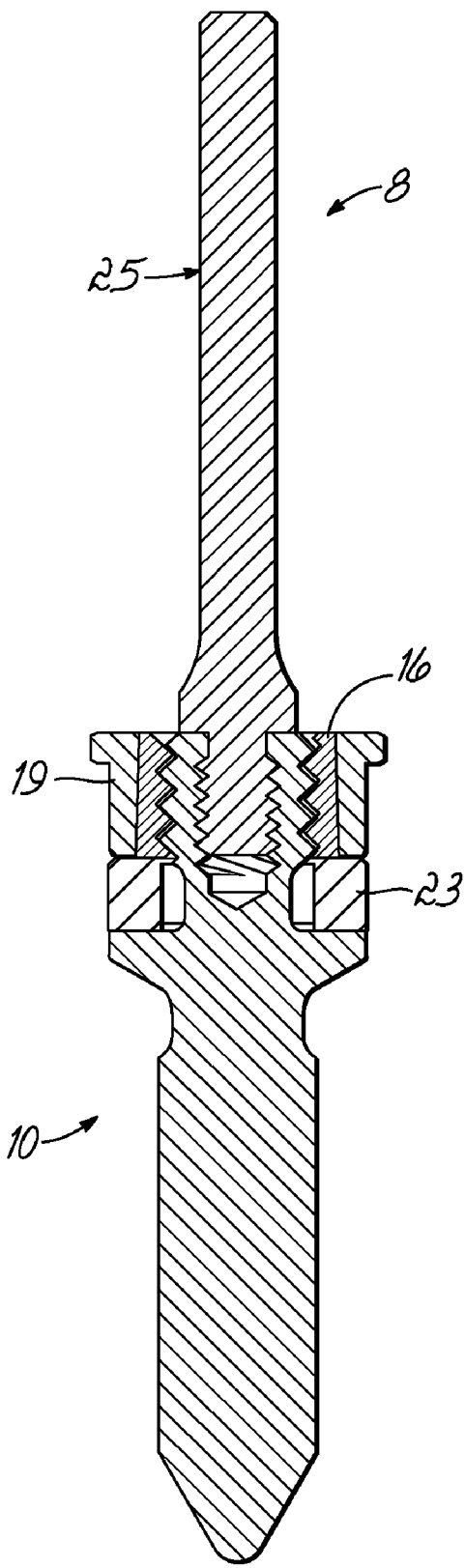
FIG. 2 is a cross-sectional view illustrating the spinal fixation assembly of FIG. 1 in a finally clamped orientation.

FIGS. 1 and 2 show a bone fixation assembly 8 having features that are examples of inventive aspects in accordance with the principles of the present disclosure. The bone fixation assembly 8 includes a bone implant 10 adapted to be secured to a bone such as a vertebral body. The bone fixation assembly 8 also includes a connector 23 such as a plate, rod or other structure adapted for linking two or more bone implants together to form a stabilizing construct. The connector 23 is secured to the bone implant 10 by a split ring 16 or sleeve. A compression ring 19 or sleeve is adapted to be slid linearly over the exterior of the split ring 16 to compress the split ring 16 radially inwardly from a pre-clamped position (shown in FIG. 1) to a final clamped orientation (shown in FIG. 2). In the final clamped orientation, the connector 23 is compressed between the split ring 16 and the bone implant 10 to limit or resist movement of the connector 23. An instrument 90 (shown in FIG. 3) can be used to minimize the amount of linear force that is applied to the patient when the compression ring 19 is slid over the split ring 16. The instrument 90 is capable of applying a downward force (see arrow b in FIG. 1) to the compression ring 19 and simultaneously applying an opposite reactionary force (see arrow a in FIG. 1) to the bone implant 10.

Figure 4:
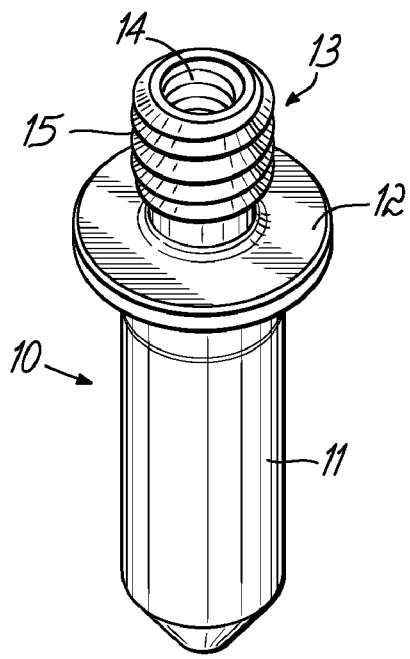
FIG. 4 is a perspective view of a bone anchor that is part of the spinal fixation assembly of FIGS. 1 and 2.

Referring now to FIG. 4, the bone implant 10 of the assembly 8 includes a bone contacting element 11 (e.g., a pedicle screw, hook, anchor or other structure adapted to be secured to a bone), a collar 12 and a hollow shank 13. The hollow shank 13 includes interior threads 14 and exterior threads 15.

Figure 5:
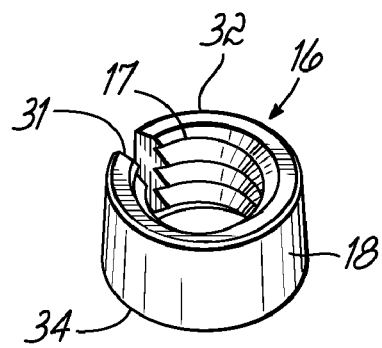
FIG. 5 is a perspective view of a split ring that is part of the spinal fixation assembly of FIGS. 1 and 2.

Referring to FIG. 5, the split ring 16 of the assembly 8 includes internal threads 17 that allow the split ring 16 to be threaded over the external threads 15 of the hollow shank 13. An external surface 18 of the split ring 16 is tapered. For example, as shown in FIGS. 1 and 5, the split ring has a truncated conical shape with a first end 32 of the split ring 16 defining a minor exterior diameter and a second end 34 of the split ring 16 defining a major exterior diameter. The split ring 16 also defines a split or gap 31 that preferably extends completely through the split ring 16 from the first end 32 to the second end 34.

Figure 6:
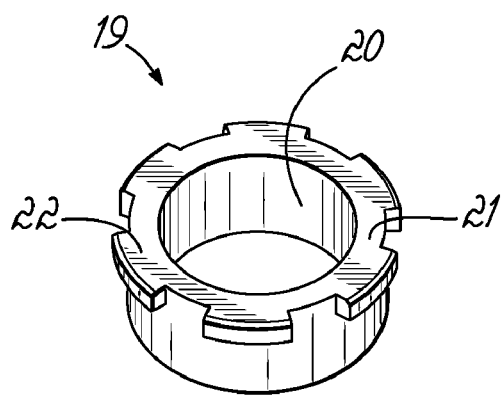
FIG. 6 is a perspective view of a compression ring that is part of the fixation assembly of FIGS. 1 and 2.

Referring to FIG. 6, the compression ring 19 of the fixation assembly 8 has a tapered interior surface 20 that is complimentary to the exterior taper of the split ring 16. In one embodiment, the tapers can comprise Morse Tapers or other type of retaining tapers for retaining the compression ring 19 on the split ring 16 once the compression ring 19 has been inserted over the split ring 16. The compression ring 19 also has a flange 21 about the upper edge. The flange 21 has lugs 22 formed in a C-shape for engaging an extractor (not shown) used to remove, or disconnect the compression ring 19 from the split ring 16.

Figure 7:
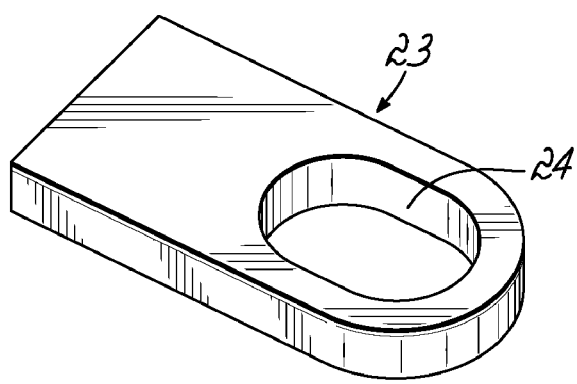
FIG. 7 is a perspective view of a connector plate that is part of the fixation assembly of FIGS. 1 and 2.

The connector 23 of the fixation assembly represents any ancillary apparatus, which would be held in place by the implant 10. As shown in FIG. 7, the connector 23 has an aperture 24 that accommodates the shank 13 and secures the connector 23 to the implant 10. The connector 23 rests on the collar 12 of the implant 10.

In certain embodiments, the connector could be a component of a set of spinal rods or spinal plates.

Figure 3:
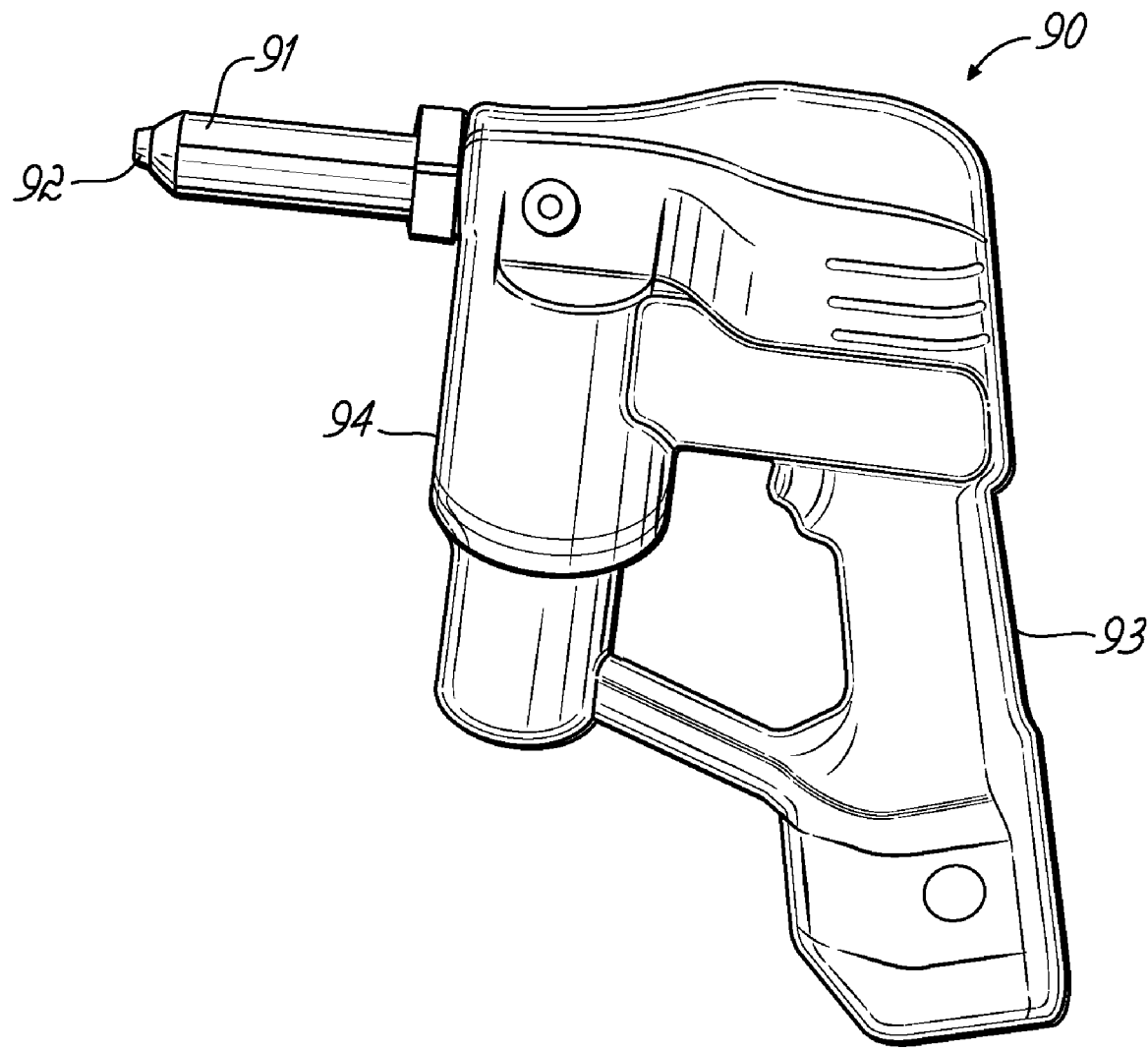
FIG. 3 is a perspective view of tool adapted for use in moving the spinal fixation assembly of FIGS. 1 and 2 from the non-finally clamped orientation to the finally clamped orientation.

Referring to FIG. 3, the driver instrument 90 is depicted having a pistol grip 93, a power source 94 and concentric pistons 91 and 92. Piston 92 is sized to grip a compression rod 25 (shown in FIG. 1) having external threads 26 and an elongated extension 27. The external threads 26 are threaded within the internal threads 14 defined within the hollow shank 13 of the bone implant 10. Piston 91 is sized to seat on the compression ring 19. In use, piston 91 applies a downward force (indicated by arrow b in FIG. 1) on the compression ring 19, while the piston 92 applies a reactionary force (indicated by arrow a in FIG. 1) to the compression rod 25. The forces a and b are in opposite directions and are preferably balanced against one another such that minimal force is applied to the patient. The rod 25 can be configured to break at the limit of optimum pressure. Alternatively, the instrument 90 may have a gauge for setting the desired pressure.

Figure 1A:
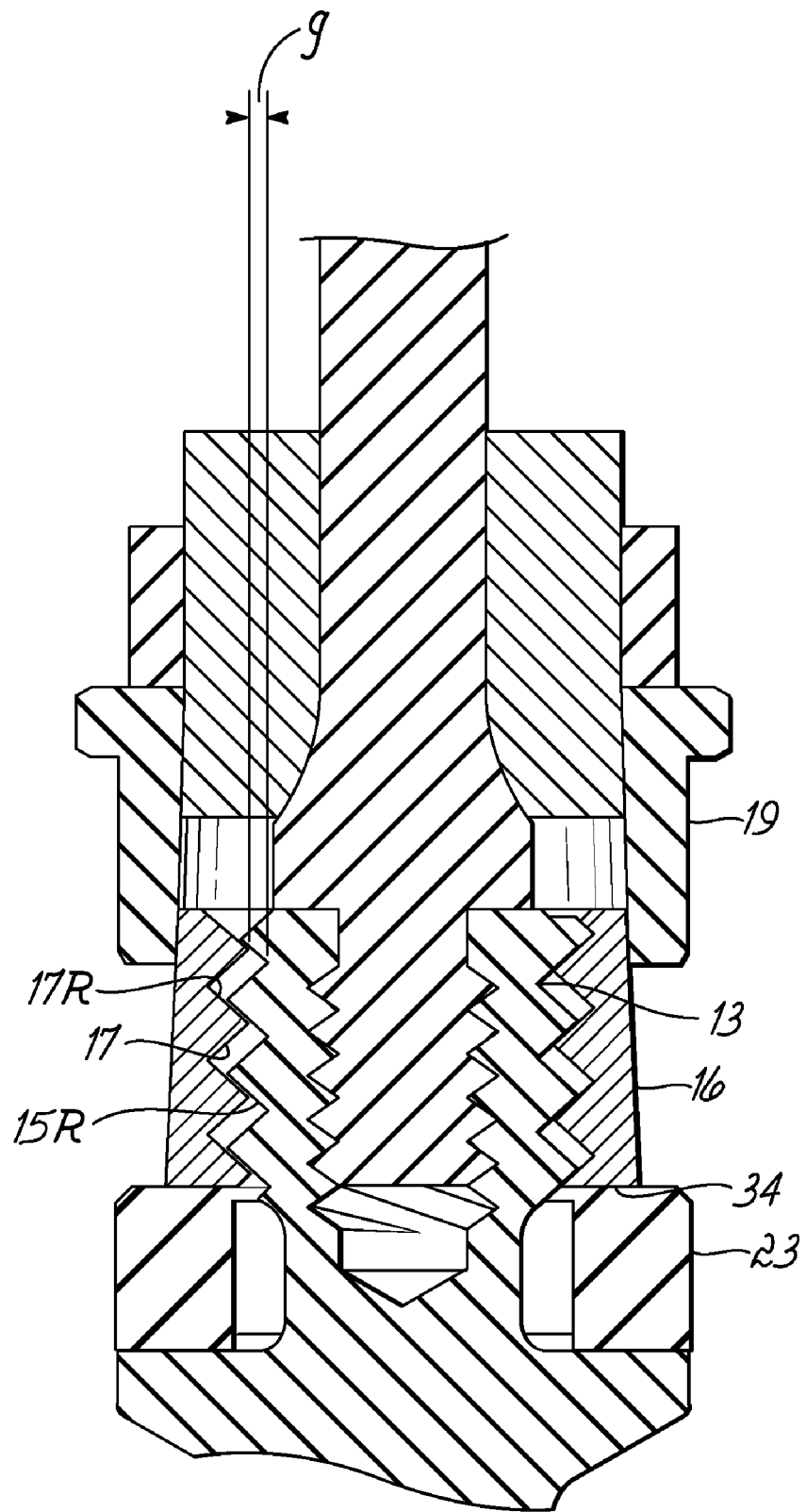
FIG. 1A is an enlarged detailed view of a portion of FIG. 1.
Figure 2A:
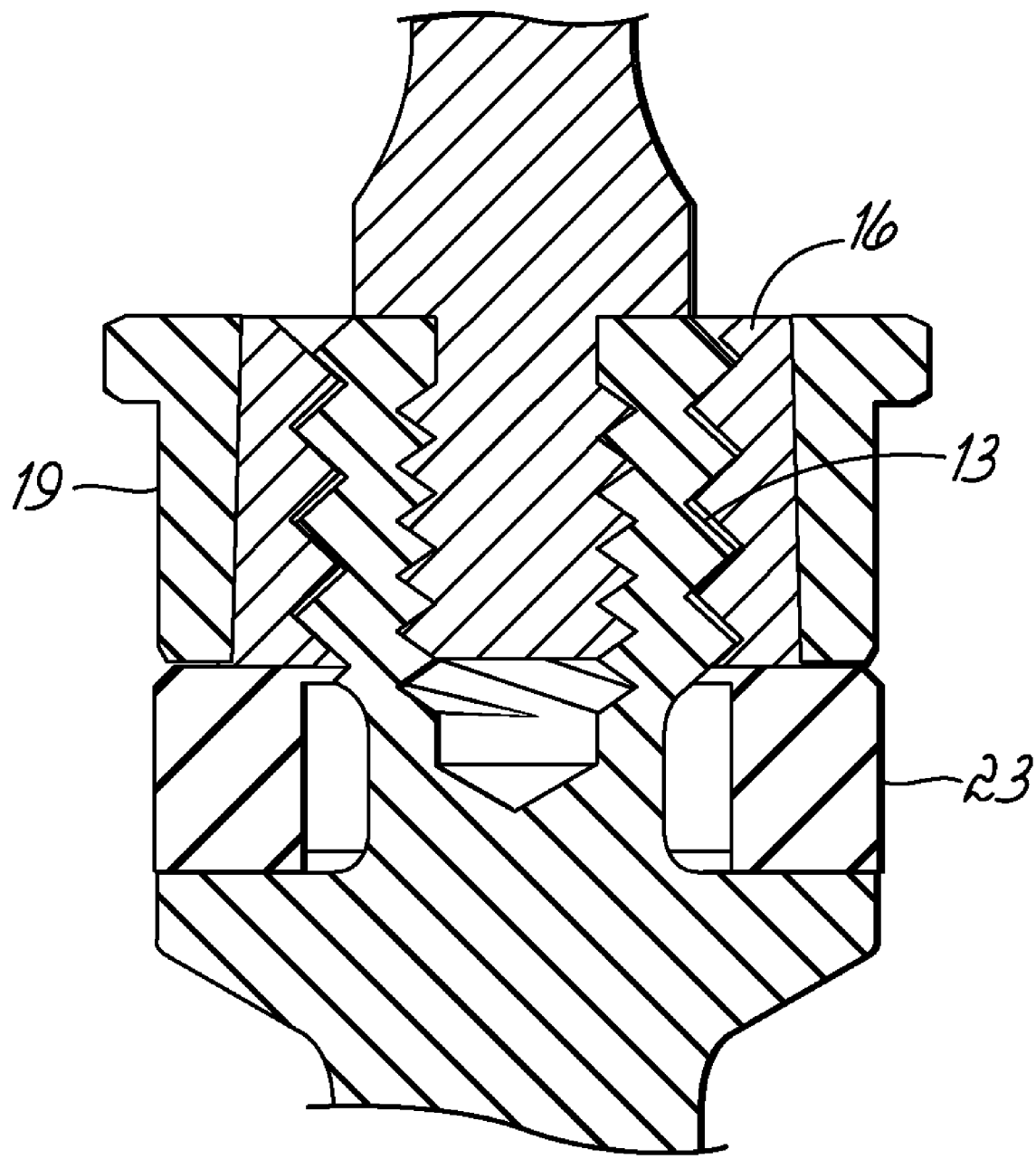
FIG. 2A is an enlarged detailed view of a portion of FIG. 2.

Referring to FIG. 1A, the interior threads 17 of the split ring 16 include ramp surfaces 17R that face upwardly and oppose corresponding ramp surfaces 15R defined by the exterior threads 15 of the shank 13. When the split ring 16 is hand-tightened down on the shank 13 into snug engagement with the connector 23, the split ring 16 is forced upwardly relative to the shank 13 such that the ramp surfaces 17R of the split ring 16 are moved into contact with the ramp surfaces 15R of the shank 13 as shown in FIG. 1A. When the compression ring 19 is inserted over the split ring 16 while the split ring is in the hand-tightened orientation of FIG. 1A, the relative tapers of the split ring 16 and the compression ring 19 cause the split ring 16 to be compressed radially inwardly. As the split ring 16 is compressed radially inwardly, the diameter of the split ring 16 reduces and a gap g between the exterior threads 15 of the shank 13 and the interior threads 17 of the split ring 16 closes. As the gap g closes, the ramp surfaces 15R of the shank 13 ride upwardly over the ramp surfaces 17R of the split ring 16 causing the shank 13 to be placed in tension (i.e., stretched) and the lower end 34 of the split ring 16 to be compressed securely against the connector 23. FIG. 2A shows the fixation assembly after the compression ring 19 has been fully inserted over the split ring 16 and the gap g substantially closed. When in the final clamped position of FIGS. 2 and 2A, the split ring 16 applies an axial load to the connector 23, generated by the tension in the shank 13, which resists movement of the connector 23. Additionally, the compression ring 19 is in radial tension causing the split ring 16 to continue to apply a radial compressive load to the shank 13 which generates friction that resists back rotation of the split ring 16 that could cause loosening of the split ring 16. In other words, once the compression ring 19 is inserted over the split ring 16, the compression ring 19 is tensionally loaded so as to maintain an inwardly directed radial compressive force, resulting in a connection that is resistant to undesired loosening.

The fixation assembly preferably includes a first structure (e.g., the tapered interface between the interior of the compression ring 19 and the exterior of the split ring 16) that converts linear force from the linear driver 90 into radial force applied to the split ring 16. The fixation assembly also preferably includes a second structure (e.g., the engaging ramp surfaces that provide an interface between the interior of the split ring 16 and the exterior of the shank 13) that converts radial force back into linear/axial force that is used to clamp the connector 23 between the split ring 16 and the collar 12.

It will be appreciated that the bone implant 10, the connector 23, the compression sleeve 19 and the split ring 16 are preferably made of a biocompatible material. A preferred material includes a metal material such as titanium. Other example materials include nitinol, stainless steel, thermal plastic polymers, thermal set polymers as well as other materials.

It is preferred for the split ring 16 to apply an axial compressive load to the plate 23 that is sufficiently large to substantially resist movement of the connector 23 relative to the bone implant 10. In one embodiment, when the compression ring 19 is compressed over the split ring 16, the split ring generates an axial load on the connector 23 that is comparable to tightening the split ring 16 with at least 20 inch pounds of torque. In another embodiment, the split ring 16 generates a compressive load comparable to that generated by tightening the split ring 16 with at least 50 inch pounds of torque. In still another embodiment, the split ring 16 generates an axial load comparable to tightening the split ring 16 with at least 100 inch pounds of torque.

It will be appreciated that the compressive load generated by the split ring is dependent upon a number of factors. Example factors include the depth of the intermeshing threads and the distance of the gap g, the angles of the ramp surfaces, and the materials used to make the bone implant 10 and the split ring 16. In one non-limiting embodiment, the gap g is at least 0.005 inches. In another non-limiting embodiment, the gap g is at least 0.01 inches. In a further non-limiting embodiment, the gap is at least 0.015 inches. In still another non-limiting embodiment, the gap is at least 0.02 inches.

Figure 8:
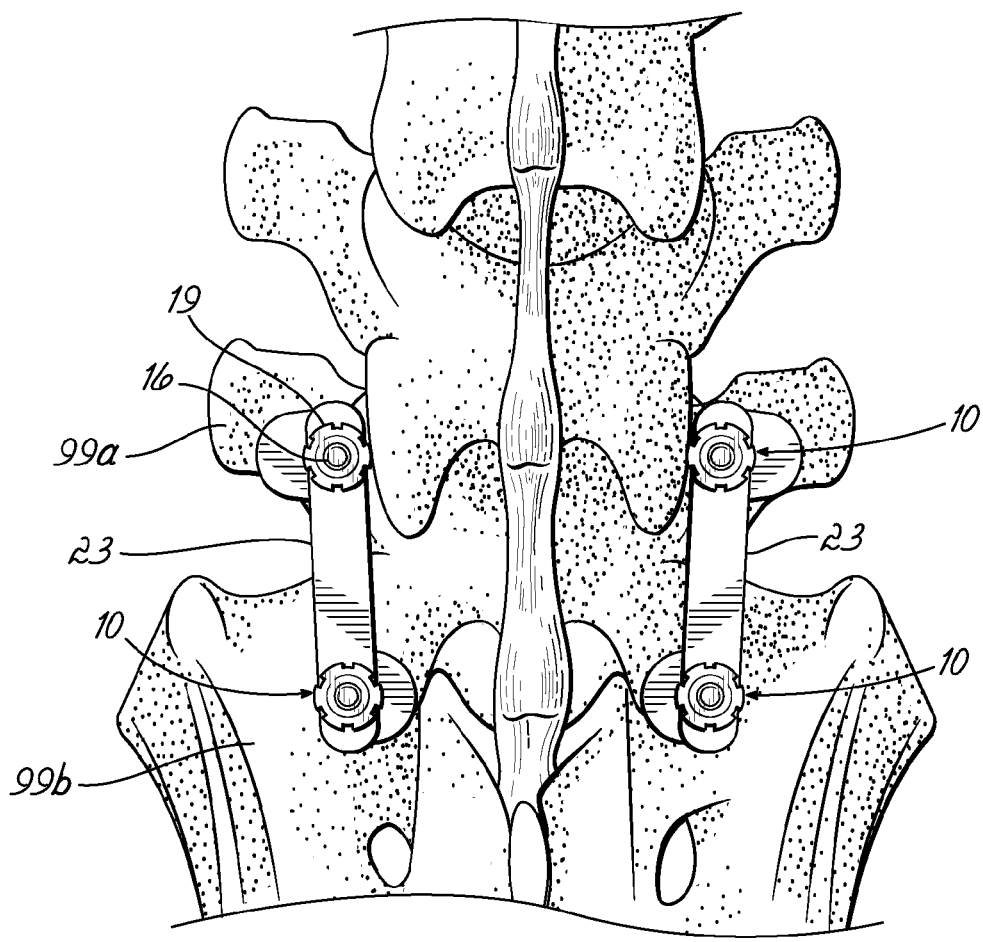
FIG. 8 is a plan view of a spinal stabilization construct incorporating fixation assemblies of the type depicted in FIGS. 1 and 2.

FIG. 8 shows a spine stabilization construct incorporating a plurality of the bone implants 10. The construct is shown being used in a single level spinal stabilization procedure. In conducting the procedure, the bone implants 10 are secured to vertebral bodies 99a and 99b. Connectors 23 are then mounted to the bone implants 10. As shown in FIG. 8, the connectors 23 are positioned on opposite sides of the patient's sagittal plane and extend across a space between the vertebral bodies 99a, 99b. After placement of the connectors 23, the surgeon can loosely thread the split rings 16 on the shanks 13 of the bone implants 10 such that the connectors 23 are provisionally retained in place. In one embodiment, the split rings 16 are finger tightened on the threaded shanks 13. In another embodiment, a torque wrench can be used to loosely tighten the split rings 16 to a provisionally tightened position. For example, in one embodiment, a torque wrench can be used to apply about 2 inch pounds of torque to the split ring 16.

After provisional tightening of the construct, the surgeon can adjust the relative positioning of the vertebral bodies 99a, 99b, to achieve a desired relative positioning. For example, the vertebral bodies 99a, 99b may be compressed together, distracted apart or moved laterally relative to one another. During distraction or compression, the connectors 23 can move relative to the anchors 10 to accommodate the adjustment and relative positioning of the vertebral bodies 99a, 99b. Once a desired spatial relationship between the vertebral bodies 99a, 99b is achieved, the connectors 23 are finally locked or clamped relative the anchors 10 through the use of the compression rings 19. For example, the tool 90 can be used to force the compression rings 19 over the exterior of the split rings 16. When the split rings 16 are compressed by the compression rings 19, the split rings 16 are caused to finally clamp the connectors 23 in position relative to the anchors 10 by axially compressing the connectors 23 between the split rings 16 and the collars 12 of the implants 10. The use of the tool 90 to linearly slide the compression rings 19 over the split rings 16 allows the construct to be finally tightened without requiring torque and without having substantial amounts of linear force transferred to the patient. While FIG. 8 shows a single level spinal stabilization procedure, it will be appreciated that constructs in accordance with the principles of the present disclosure can be used in multi-level procedures as well as other types of stabilization procedures.

In the event that the construct must be disassembled, removal instruments similar to the driver instrument 90 may be employed. The removal instrument would include a piston having a flange with flat lugs. The instrument would be placed over the compression ring and turned to engage the flat lugs. Once the flat lugs are engaged, an upward force can be applied to the compression ring to remove it from the split ring 16. Simultaneously, an inner piston would apply a downward force to the shank 13 of the bone anchor 10 such that minimal net force is transferred to the patient. Once the compression rings 19 are removed, the split rings 16 can be manually unthreaded from the shanks 13 to allow the construct to be disassembled.

Figure 9:
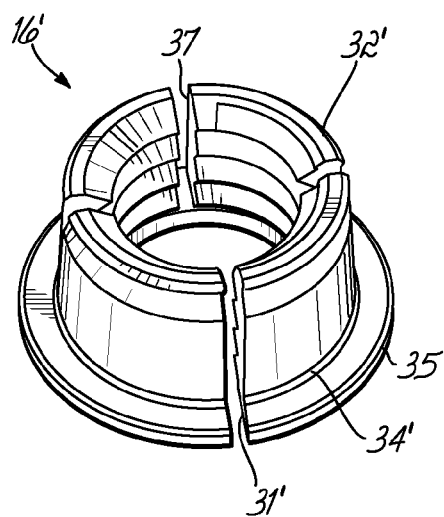
FIG. 9 is a perspective view of an alternative compression ring adapted for use with the fixation assembly of FIGS. 1 and 2.

Referring to FIG. 9, an alternative split ring 16' adapted for use with the bone anchor 10 is depicted. The split ring 16' is internally threaded and includes an external surface that is conically tapered and defines a minor exterior diameter at a first end 32' and a major exterior diameter at a second end 34'. A radial flange 35 is provided at the second end 34'. The flange 35 may function as a flared base suitable to distribute clamping forces over a wide area or to provide a bearing surface for resisting relative rotation of adjacent components. The split ring 16' further includes a plurality of partial slots 37 that extend only partially through the split ring 16' between the first and second ends 32' and 34', and one full slot 31'.

Figure 10:
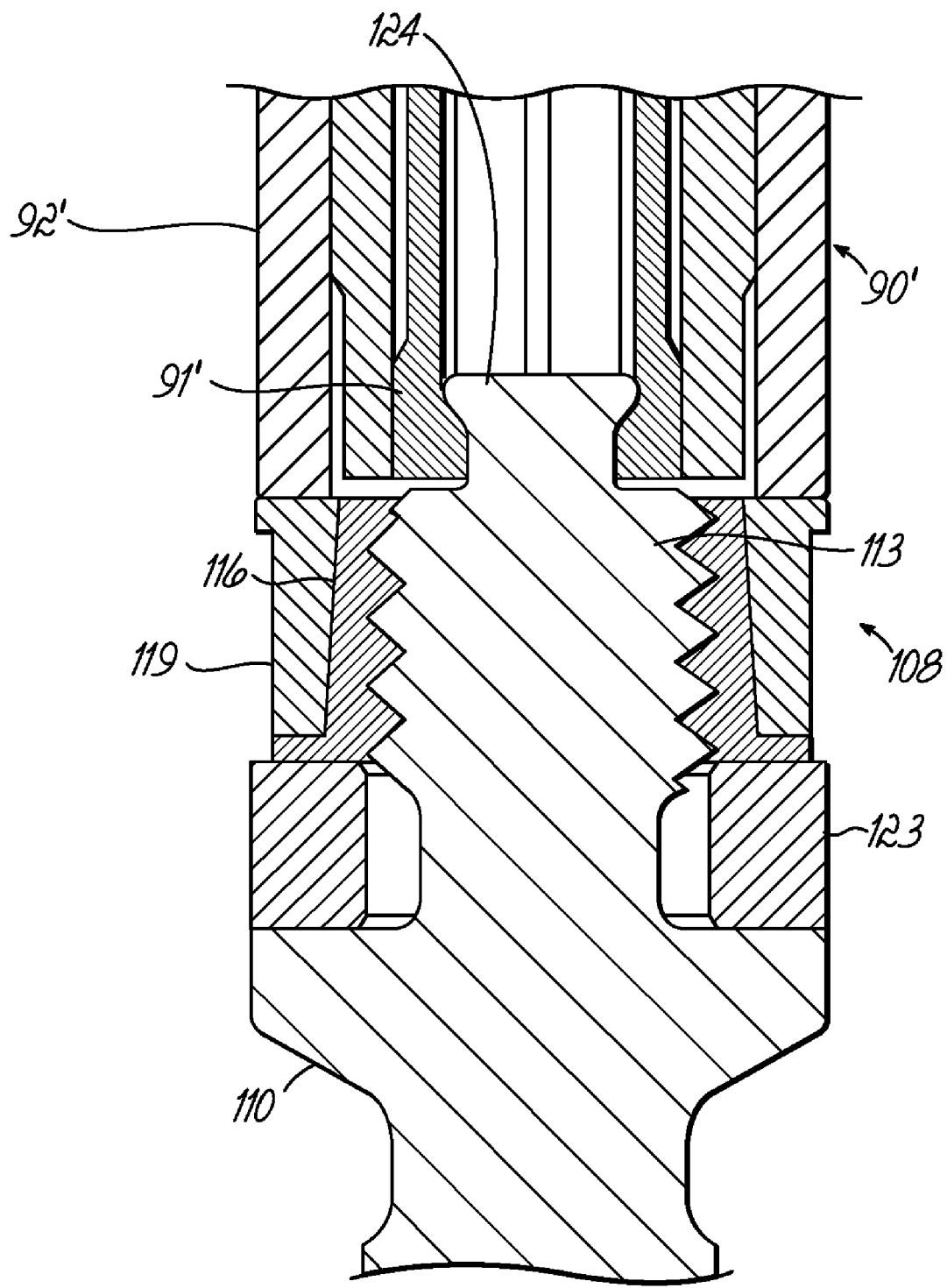
FIG. 10 is a cross-sectional view illustrating a second embodiment of a spinal fixation assembly having features that are examples of inventive aspects in accordance with the principles of the present disclosure.

FIG. 10 shows an alternative fixation assembly 108 having a bone anchor 110, a connector 123, a split ring 116 and a compression ring 119. The fixation assembly 108 has the same configuration as the fixation assembly 8, except the bone anchor 110 has been modified to provide a different interface for providing a connection with a linear driver tool. Specifically, rather than providing an internal bore within a shank 113 of the bone anchor 110, the bone anchor includes an enlarged tip 124 or projection constructed and arranged to be grasped by a linear driver tool 90'. The driver tool 90' includes an interior driver member 91' that grasps the tip 124 and an outer driver member 92' adapted to push downwardly on the compression sleeve 119. In use, the outer driver member 92' pushes downwardly on the compression sleeve 19 while the interior driver member 91' applies an opposite force to the shank of the bone implant 10 such that the net linear force transferred to the patient is minimal.

FIGS. 11-13 illustrate an alternative fixation assembly 208 having features that are examples of inventive aspects in accordance with the principles of the present disclosure. The fixation assembly 208 operates in a manner similar to the fixation assembly 8 of FIGS. 1 and 2, and includes a bone anchor 210, a connector 223, a split ring 216 and a compression ring 219. The assembly 208 is substantially the same as the fixation assembly 8, except the interface between the split ring 216 and the exterior surface of the shank 213 of the bone implant 210 has been modified. For example, rather than having intermating threads, the fixation assembly 208 includes non-threaded ramp surfaces that ramp against one another when the assembly is finally clamped.

Referring to FIG. 12, the shank 213 of the bone implant 210 includes a downwardly facing ramp surface 215 located adjacent to a head 250 of the shank 213. The ramp surface 215 cooperates with an upwardly facing ramp surface 217 provided at the top end of the split ring 216. When the compression ring 219 is linearly slid axially over the exterior of the split ring 216, the split ring 216 is compressed radially inwardly (as shown in FIG. 13) causing the ramp surface 215 of the shank to ride over the ramp surface 217 of the split sleeve 216. The interaction of the ramp surfaces converts radial force applied by the compression ring 219 into a linearly/axially directed force which causes the shank 213 to be placed in tension and the split ring 216 to be compressed firmly against the connector 223 such that the connector 223 is finally clamped in place relative to the bone implant 210. FIG. 12 shows the fixation assembly prior to sliding the compression ring into the finally clamped orientation. FIG. 13 shows the fixation assembly in the finally clamped orientation. A tool that limits or eliminates the linear force transferred to the patient can be used to force the compression ring 219 over the split sleeve 216.

Figure 14:
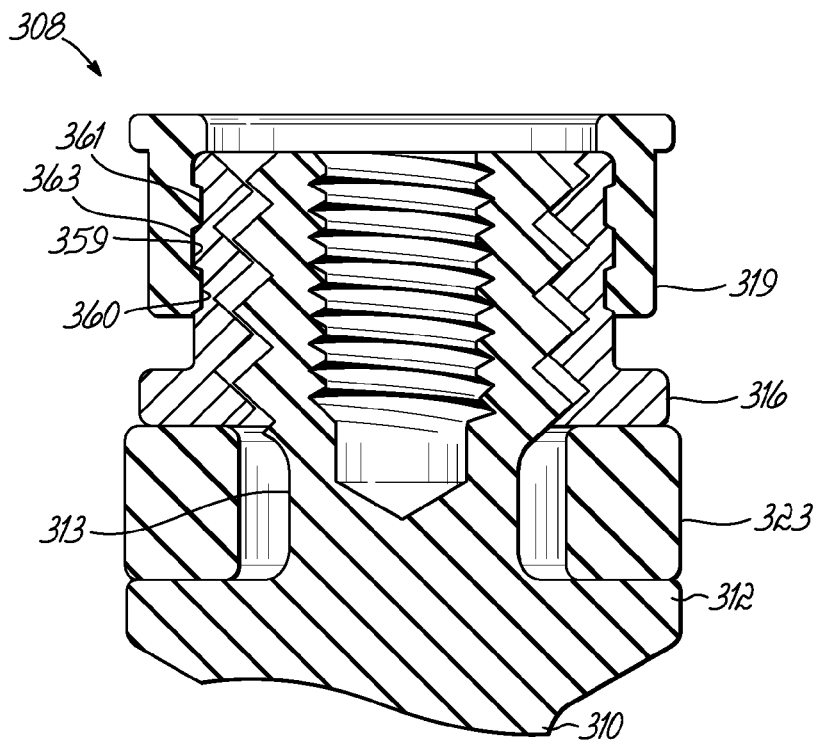
FIG. 14 is a cross-sectional view illustrating a fourth embodiment of a spinal fixation assembly having features that are examples of inventive aspects in accordance with the principles of the present disclosure, the assembly is shown in a non-finally clamped orientation.
Figure 15:
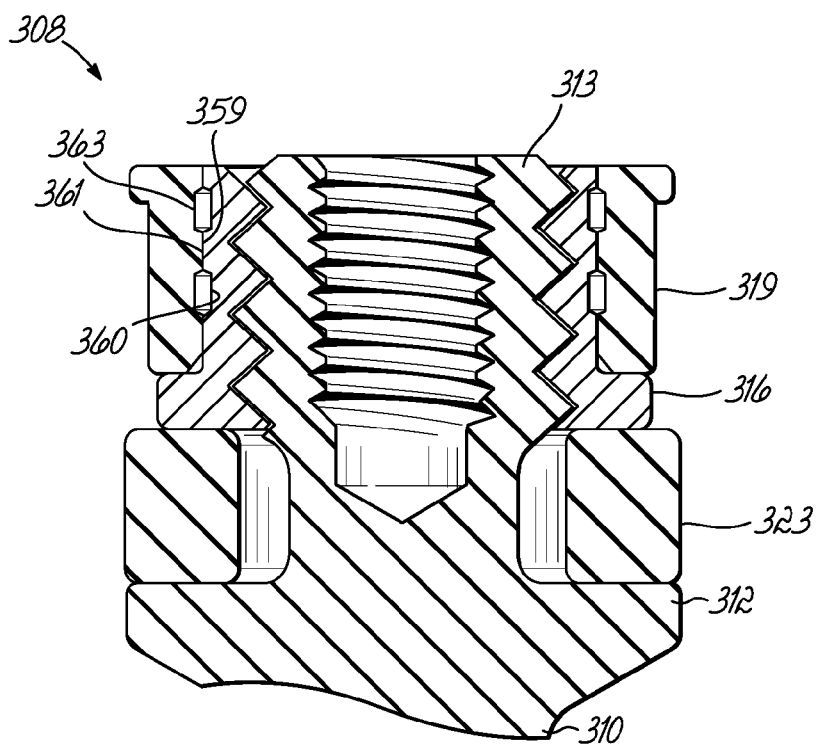
FIG. 15 is a cross-sectional view showing the fixation assembly of FIG. 14 in a finally clamped orientation.

FIGS. 14 and 15 show still another embodiment of a fixation assembly 308 having features that are examples of inventive aspects in accordance with the principles of the present disclosure. The fixation assembly 308 has the same basic components and operates under the same principles as the fixation assembly 8 of FIGS. 1 and 2. For example, similar to the fixation assembly of FIGS. 1 and 2, the fixation assembly includes a bone implant 310, a connector 323, a split ring 316 and a compression ring 319. The bone implant includes an anchor (e.g., a pedicle screw, hook, rivet, or other structure), a shoulder 312 and a shank 313 having internal and external threads. The split ring 316 has internal threads that mate with the external threads of the shank 313. However, the embodiment of FIGS. 14 and 15 has been modified to include a different interface between the interior surface of the compression ring 319 and the exterior surface of the split ring 316. For example, the split ring 316 includes a plurality of circumferential ribs 359 that project outwardly from the exterior of the split ring 316. The ribs 359 are separated by recesses 360. Upper and lower sides of the ribs 359 are ramped. The compression ring 319 has inwardly projecting ribs 361 separated by recesses 363. The top and bottom sides of the ribs 361 are also ramped.

FIG. 14 shows the fixation assembly in a pre-clamped orientation. In this orientation, the ribs 361 of the compression ring 319 fit within the recesses 360 of the split ring 316. In this configuration, a gap exists between the interior threads of the split ring 316 and the exterior threads of the shank 313. When the compression ring 319 is forced down relative to the split ring 316 (e.g., with tool 90), the ribs 361 of the compression ring 319 ramp on to the ridges 359 of the split ring 316 causing the split ring to be compressed radially inwardly as shown in FIG. 15. As the split ring 316 is compressed radially inwardly, the outer threads of the shank 313 ramp up on the inner threads of the split ring 316 causing the shank 313 to be tensioned and also causing the split ring 316 to be compressed axially against the connector 323 such that the connector is locked in a final position relative to the bone implant 310.

The rib configuration of FIGS. 14 and 15 allow the split ring 316 and the compression sleeve 319 to be interconnected when in the pre-clamped orientation to minimize the number of loose parts. Also, the ribs allow the amount of compression generated by the linear movement of the compression sleeve 319 relative to the split ring 316 to be precisely controlled by controlling the ramp angles of the ribs as well as the distance the ribs project outwardly from the split ring 316. This configuration allows a relatively large amount of compressive force to be generated in a relatively small range of linear movement.

Figure 16:
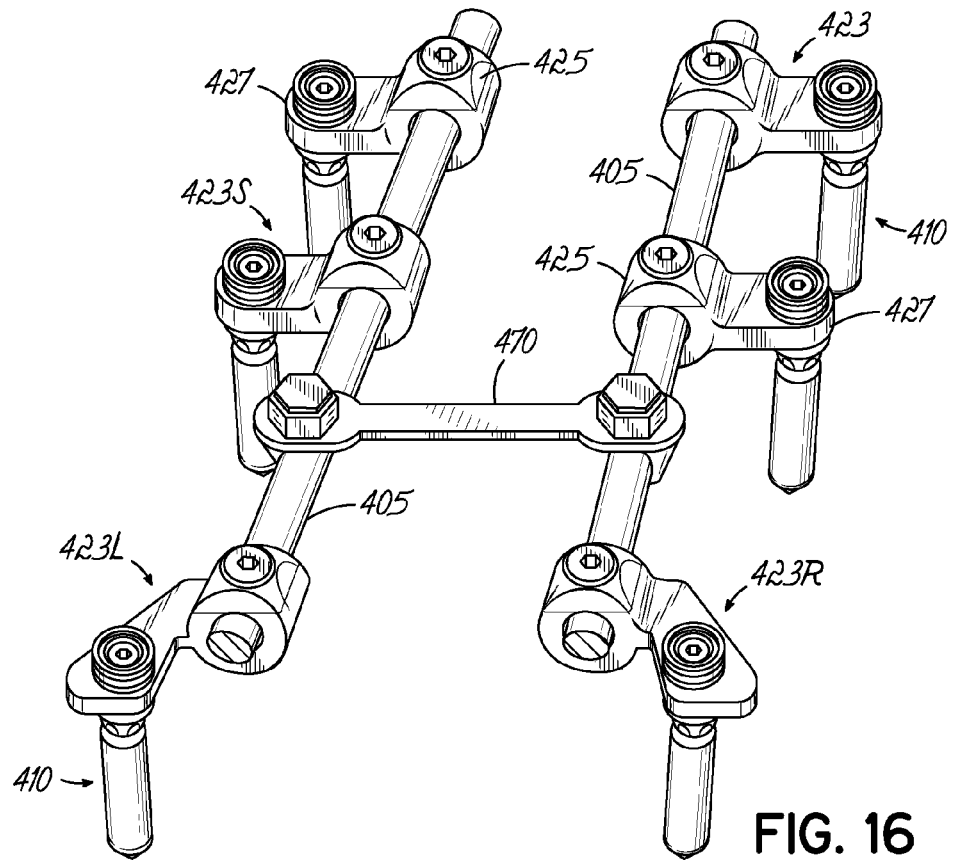
FIG. 16 is a perspective view of a bone stabilization construct including a fifth embodiment of a spinal fixation assembly having features that are examples of inventive aspects in accordance with the principles of the present disclosure.

FIG. 16 illustrates a further spine stabilization construct having inventive aspects in accordance with the principles of the present disclosure. The construct includes a pair of rods 405 adapted to be positioned on opposite sides of a patient's sagittal plane. The rods are interconnected by a transverse connector 470. The construct also includes a plurality of vertebral implants 410. The vertebral implants 410 are linked to the rods 405 by connectors 423. The connectors 423 include first ends 425 clamped to the rods 405 and second ends 427 clamped to the vertebral implants 410. The connectors 423 are depicted as left offset connectors 423L, right offset connectors 423R, and straight connectors 423S. The vertebral implants 410 are clamped to the connectors 423 through the use of fasteners that utilize linear force for final tightening. Further details regarding the connectors 423 can be found in U.S. Pat. No. 6,050,997, which is hereby incorporated by reference in its entirety.

Figure 17:
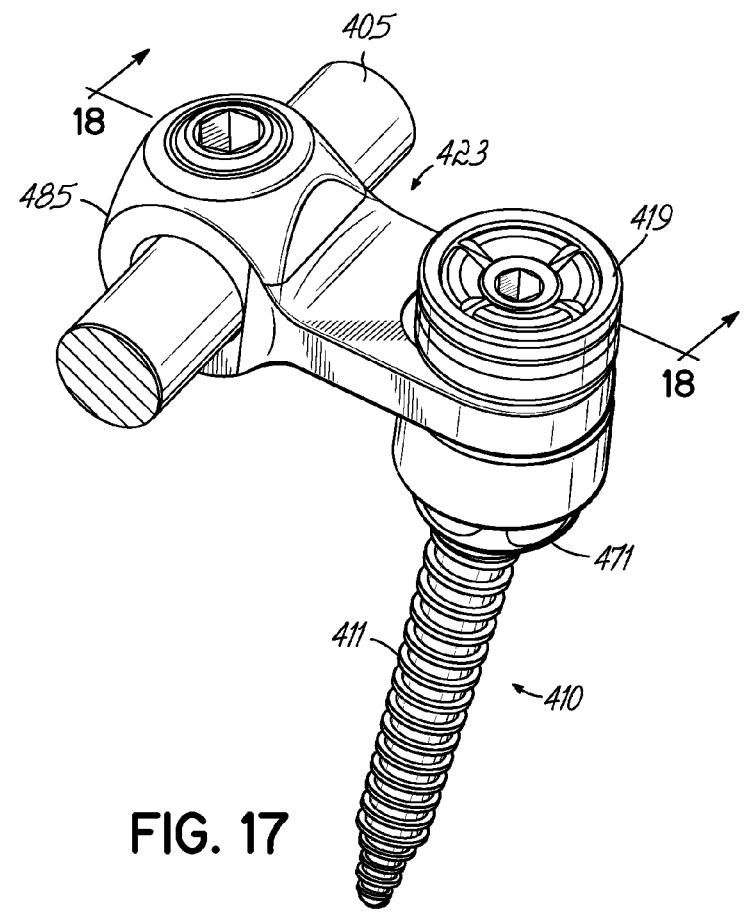
FIG. 17 is a perspective view of one of the spinal fixation assemblies of FIG. 16 in isolation from the remainder of the construct.
Figure 18:
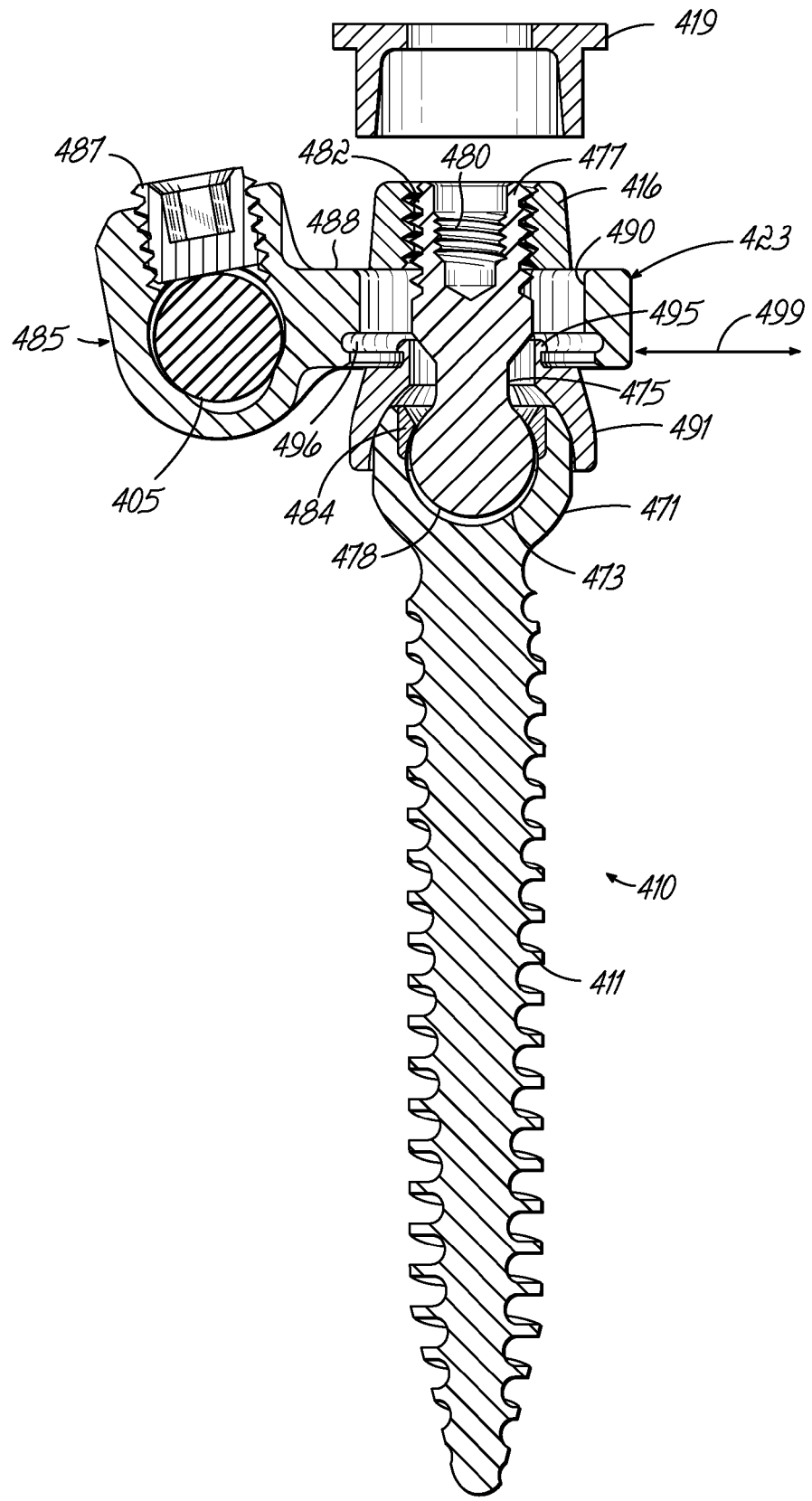
FIG. 18 is a cross-sectional view of the assembly of FIG. 17 showing the assembly in a pre-finally clamped orientation.
Figure 19:
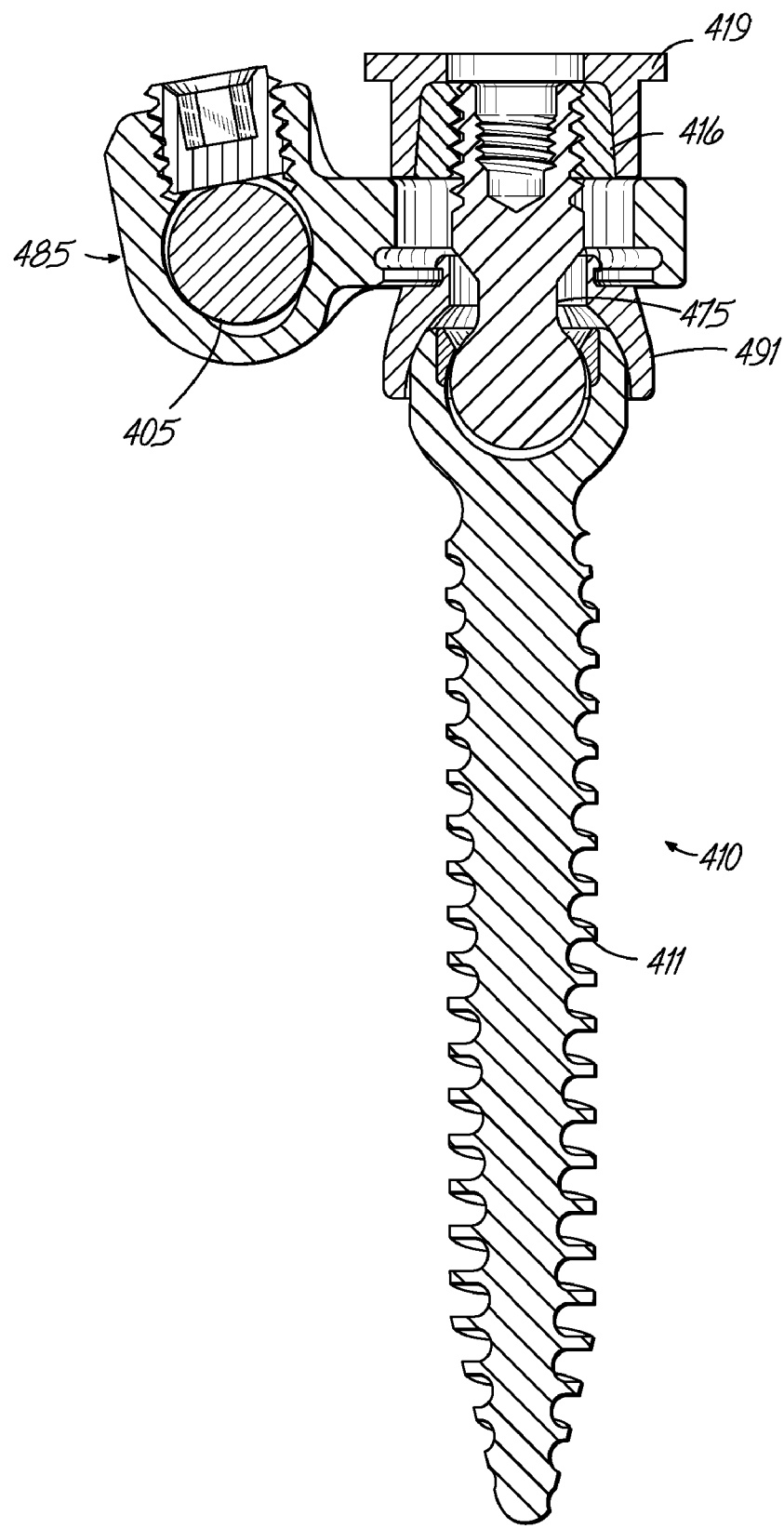
FIG. 19 is a cross-sectional view of the assembly of FIG. 17 showing the assembly in a finally clamped orientation.

Referring to FIGS. 17-19, one of the vertebral implants 410 and its corresponding connector 423 are shown in isolation from the remainder of the construct. The vertebral implant 410 is depicted including a pedicle screw 411 having a rounded head 471. A socket 473 is defined within the head 471. The implant 410 also includes a bolt 475 having a first end 477 positioned opposite from a second end 478. The first end 477 of the bolt 475 includes inner threads 480 and outer threads 482. The second end 478 of the bolt 475 includes a rounded head that pivotally mounts within the socket 473 of the screw 411 to allow for polyaxial adjustment of the bone screw 411 relative to the bolt 475. The head of the bolt 475 is retained within the socket 473 by a retainer 484. Retainer 484 can be a ring fixedly connected to the head of the screw 411 by a conventional technique such as welding. Alternatively, the retainer 484 can be a split ring that is snap-fit within the socket 473, or can be threaded within the socket 473 or otherwise connected to the head 471 of the bone screw.

The connector 423 includes a rod coupler 485 including a receptacle 486 for receiving one of the rods 405. The rod 405 is clamped within the rod coupler 485 by a set screw 487. The connector 423 also includes an extension plate 488 that projects outwardly from the coupler 485. The extension plate 488 defines an elongated through-hole 490 through which the bolt 475 extends. A collar 491 is slidably mounted to the extension plate 488 adjacent the bottom side of the through-hole 490. The collar 491 includes an upper flange 495 that fits within a groove 496 located at the bottom of the through-hole 490. The groove 496 allows the position of the collar 491 to be adjusted along the length of the through-hole 490 in a direction indicated by arrow 499. The collar 491 has an interior surface that is curved to generally match the outer curvature of the head 471 of the screw 411. Prior to tightening of the toggle bolt 475, the bone screw 411 is free to pivot relative to the head of the toggle bolt 475, and also is free to pivot relative to the collar 491.

A fastener arrangement including a split ring 416 and a compression sleeve 419 is used to tighten the bolt 475 and clamp the screw 411 in position. When the split ring 416 and compression sleeve 419 are finally locked in place as shown in FIG. 18, tension is applied to the bolt 475 causing the head 471 of the screw 411 to be securely clamped between the collar 491 and the head of the bolt 475 thereby resisting pivotal movement of the screw 411. The tensioned bolt 475 also functions to securely clamp the collar 491 against the underside of the extension plate 488 such that movement of the collar 491 along the length of the through-hole 490 is resisted. In one embodiment, the split ring 416 and the compression ring 419 can have the same general configuration as the split ring 16 and compression ring 19 of the embodiments of FIGS. 1 and 2.

In use, the bone implants 410 are secured to vertebral bodies desired to be stabilized. The connectors 423 can then be secured to the bone implants 410 by inserting the threaded ends 471 of the bolts 475 through the through-holes 490 defined by the extension plates 488 of the connectors 423. Rods 405 can the be placed through the rod couplers 485 to link the various vertebral bodies together and form a stabilizing construct. When the desired spacing between the vertebral bodies has been established and the bone screws 411 are pivoted to desired polyaxial angles, the fasteners of the construct can be tightened down to lock the construct in a final position. For example, the set screws 487 are locked down by applying torque to the tight set screws such that the rods 405 are compressed within the rod couplers 485. The bone anchors 410 are fixed relative to the connectors 423 by first loosely threading the split rings 416 on the threaded ends 477 of the bolts 475. Preferably, the split rings 416 are finger tightened or tightened with minimal torque (e.g., 2 inch pounds) with a torque wrench so as to be placed in snug engagement with the top sides of the extension plates 488 (see FIG. 18). Thereafter, the bone implants 410 are finally clamped in place relative to the connectors 423 by forcing the compression sleeves 419 over the exteriors of the split nuts 416 (see FIG. 19). As the compression sleeves 419 are pushed downwardly, the split rings 416 compress radially inwardly causing their interior threads to ramp relative to the exterior threads of the bolt 475. This ramping action generates tension along the bolts 475, which causes the heads of the bone anchors 411 to be drawn tightly against the undersides of the collars 491, and the collars 491 to be compressed against the undersides of the extension plates 488. With the bolts 475 tensioned in this manner, a clamping effect is generated which resists pivotal movement of the bone screw 411 and also resists the sliding movement of the collar 491 relative to the connector 423. As described above with respect to the embodiment of FIGS. 1 and 2, a linear diver instrument 90 can be used to force the compression ring 419 downwardly without applying a substantial amount of linear force to the patient.

Figure 20:
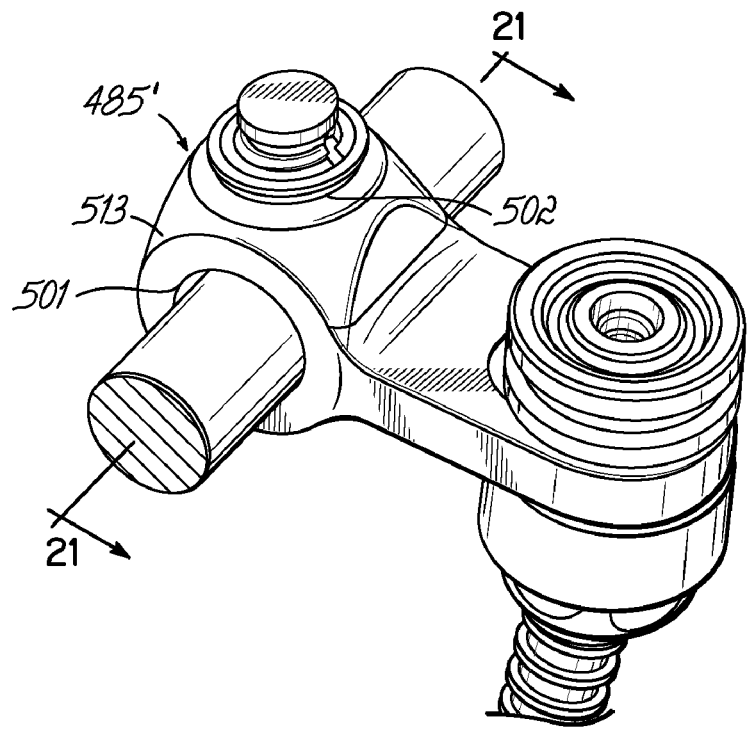
FIG. 20 is a perspective view of a sixth embodiment of a spinal fixation assembly having features that are examples of inventive aspects in accordance with the principles of the present disclosure.
Figure 21:
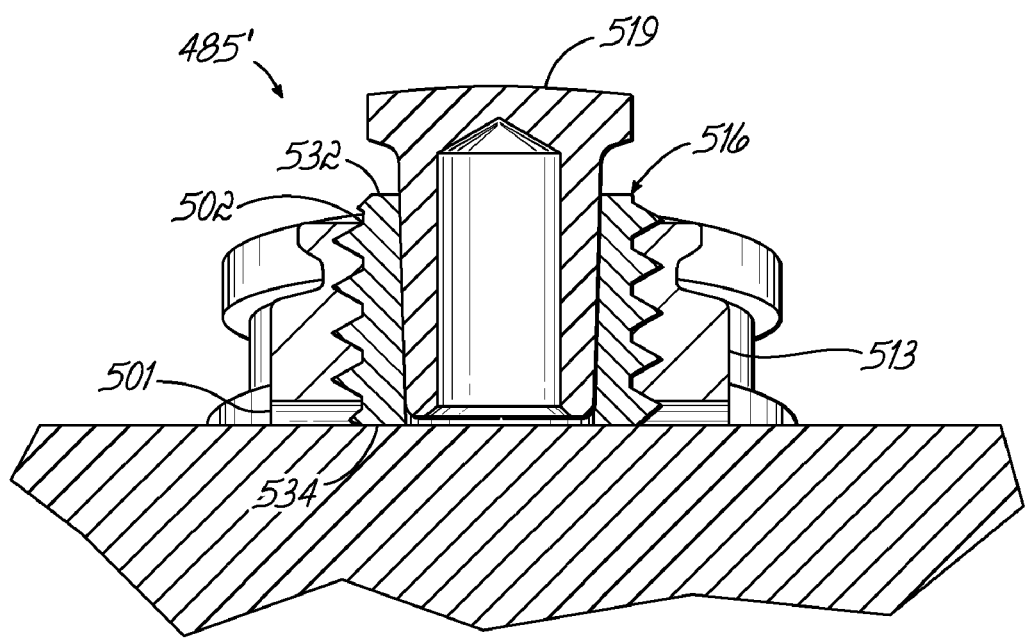
FIG. 21 is a cross-section view taken along section line 21-21 of FIG. 20 in which the spinal fixation assembly is shown in a finally clamped orientation.
Figure 22:
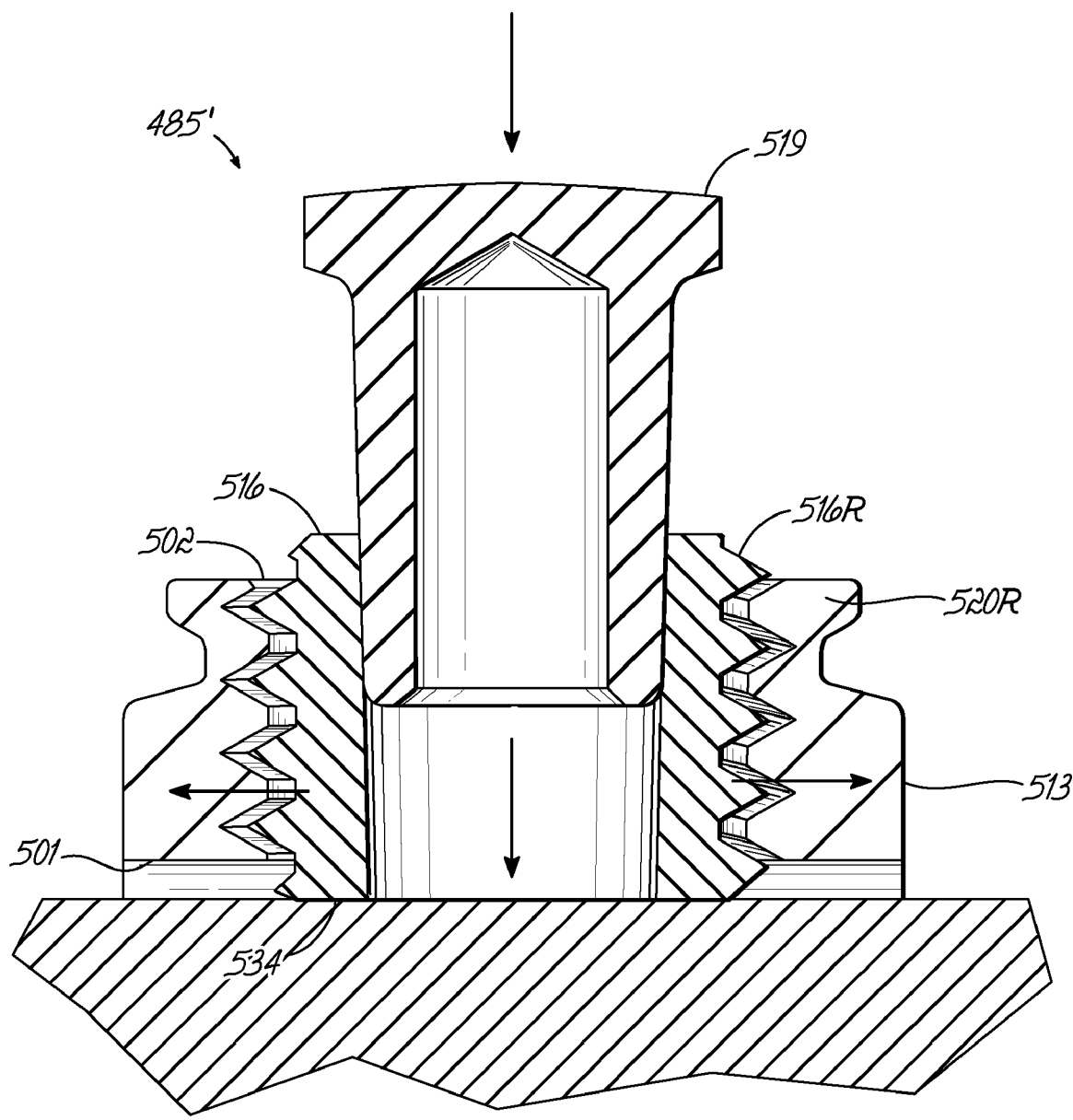
FIG. 22 is a cross-section view of the spinal fixation assembly of FIG. 21 in a non-finally clamped orientation.

In certain embodiments, the set screw 487 of the rod coupler 485 can be replaced with a fastening arrangement that is placed in a finally locked orientation through the use of linear force. FIGS. 20-22 show a rod receiver/coupler 485' adapted for use with such a fastening arrangement. The rod coupler 485' has a main body 513 that defines a horizontal through-hole 501 for receiving a spinal stabilization rod, and a vertical fastener opening 502 that extends downwardly from a top side of the main body 513 to the horizontal through-hole 501. The fastener opening 502 includes internal threads.

Figure 23:
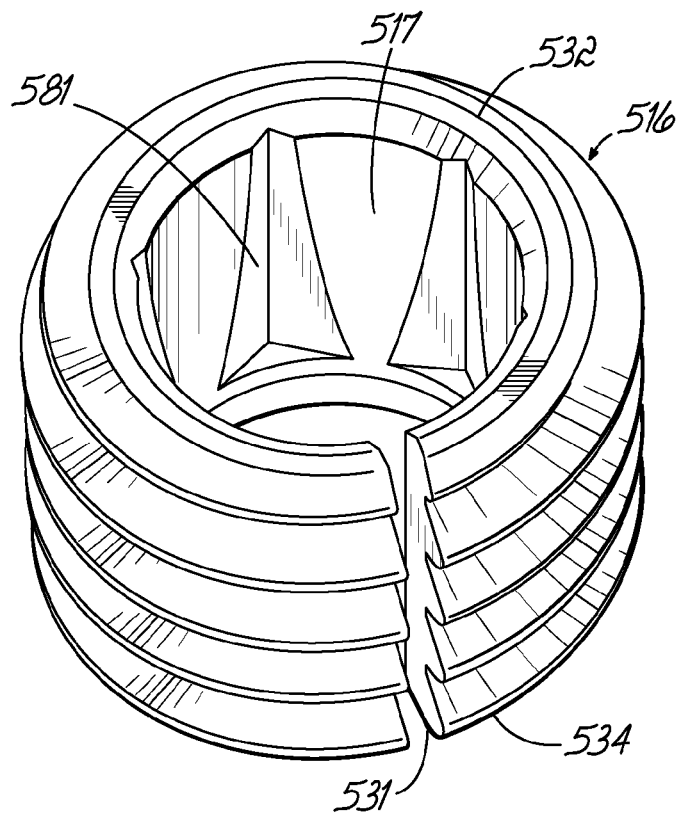
FIG. 23 is a perspective view of a split member of the spinal fixation assembly of FIG. 21.

The fastening arrangement includes a split member 516 (shown in FIG. 23) that mounts within the fastener opening 502. The split member 516 includes external threads that mate with the internal threads of the fastener opening 502. The split member 516 is sized smaller than the fastener opening 502 such that, prior to expansion of the member 516, a gap is provided between the threads of the member 516 and the threads of the fastener opening 502. The split member 516 includes a top end 532 positioned opposite from a bottom end 534. A slit 531 extends completely through the split member 516 from the top end 532 to the bottom end 534. The split member 516 also defines an interior opening 517. Preferably, the interior opening 517 is tapered such that the interior opening 517 defines a maximum interior diameter adjacent the top end 532 of the split member 516 and a minor interior diameter located adjacent the bottom end 534 of the split member 516. The interior opening 517 can also define one or more tool engaging structures 581 adapted to interface with a tool (e.g., a wrench) for allowing torque to be applied to the split member 516.

Figure 24:
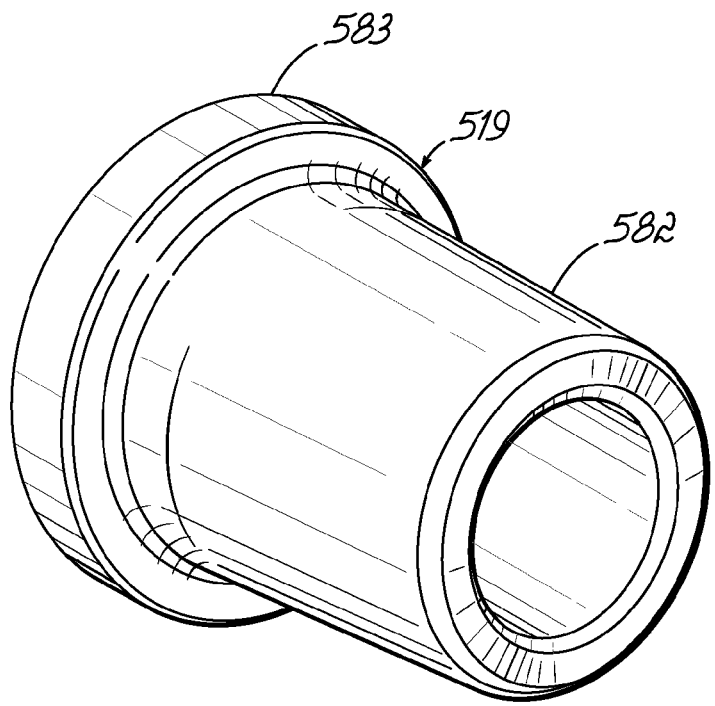
FIG. 24 is a perspective view of an expansion plug of the spinal fixation assembly of FIG. 21.
Figure 25:
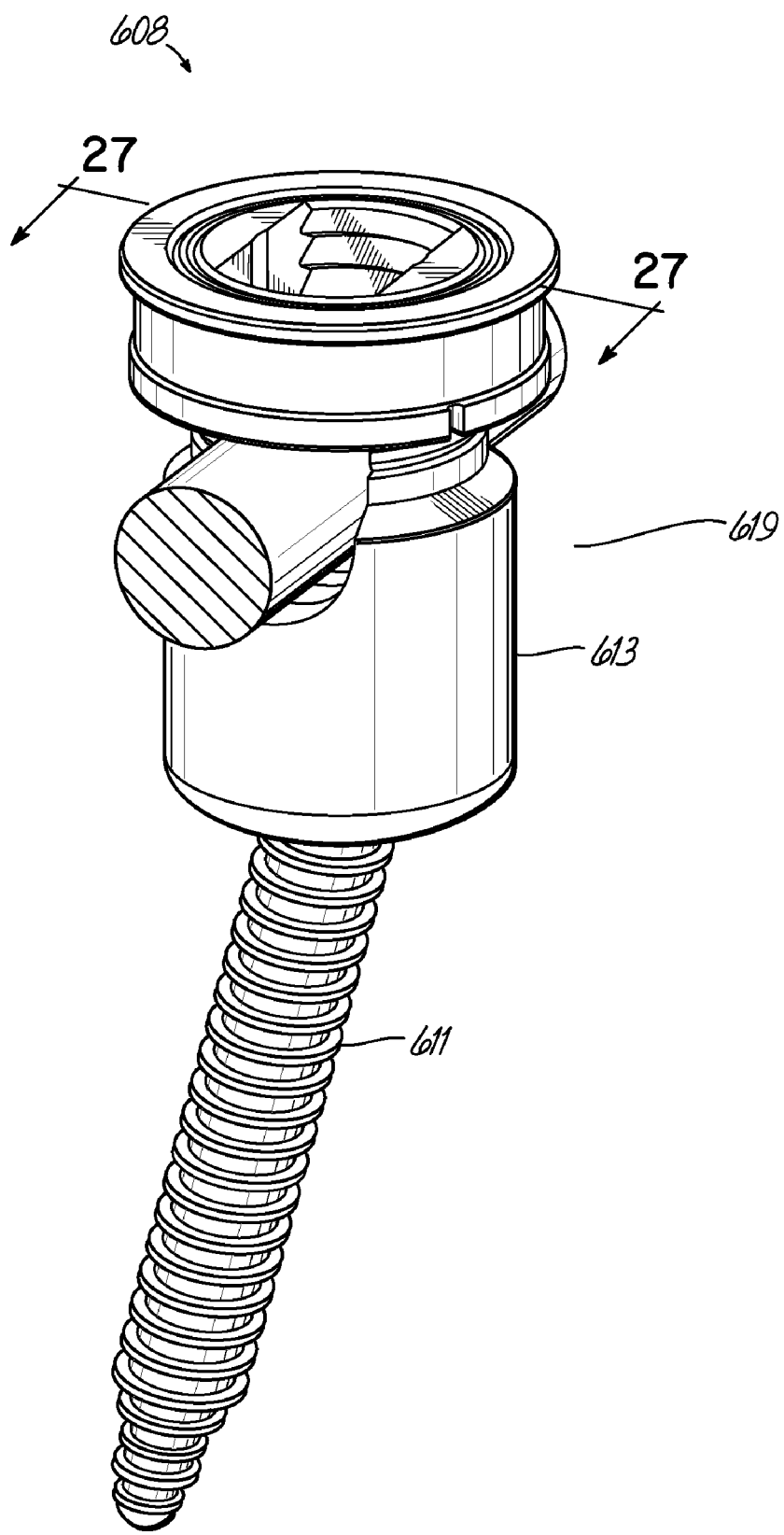
FIG. 25 is an assembled, perspective view illustrating a seventh embodiment of a spinal fixation assembly having features that are examples of inventive aspects in accordance with the principles of the present disclosure.
Figure 26:
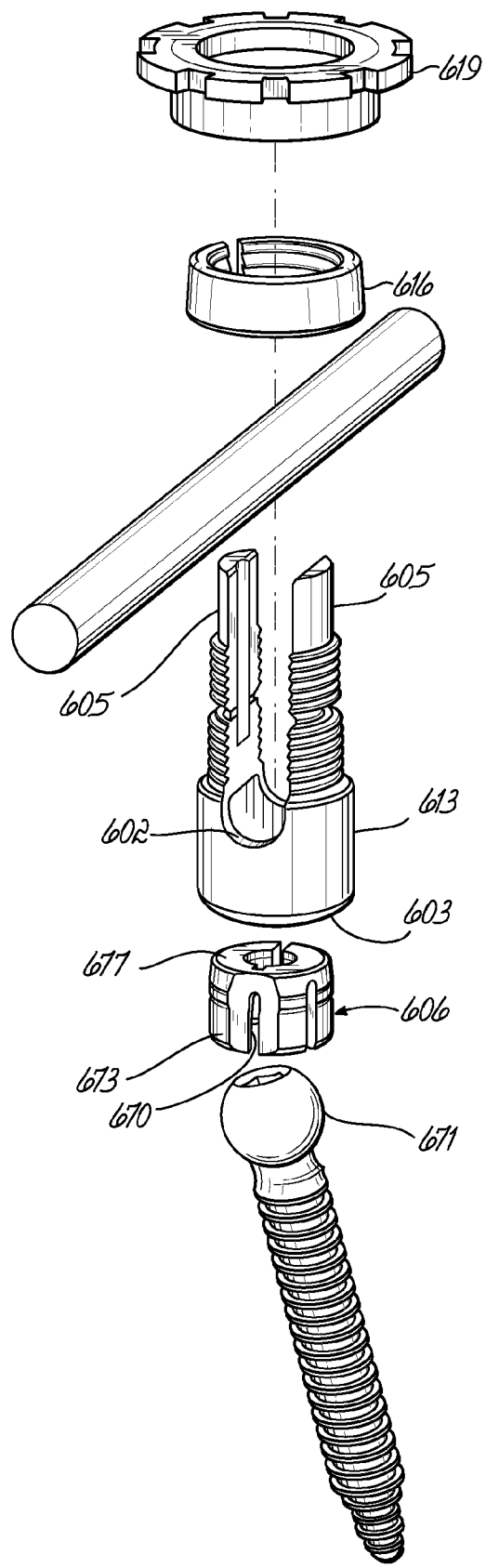
FIG. 26 is an exploded, perspective view of the spinal fixation assembly of FIG. 25.
Figure 27:
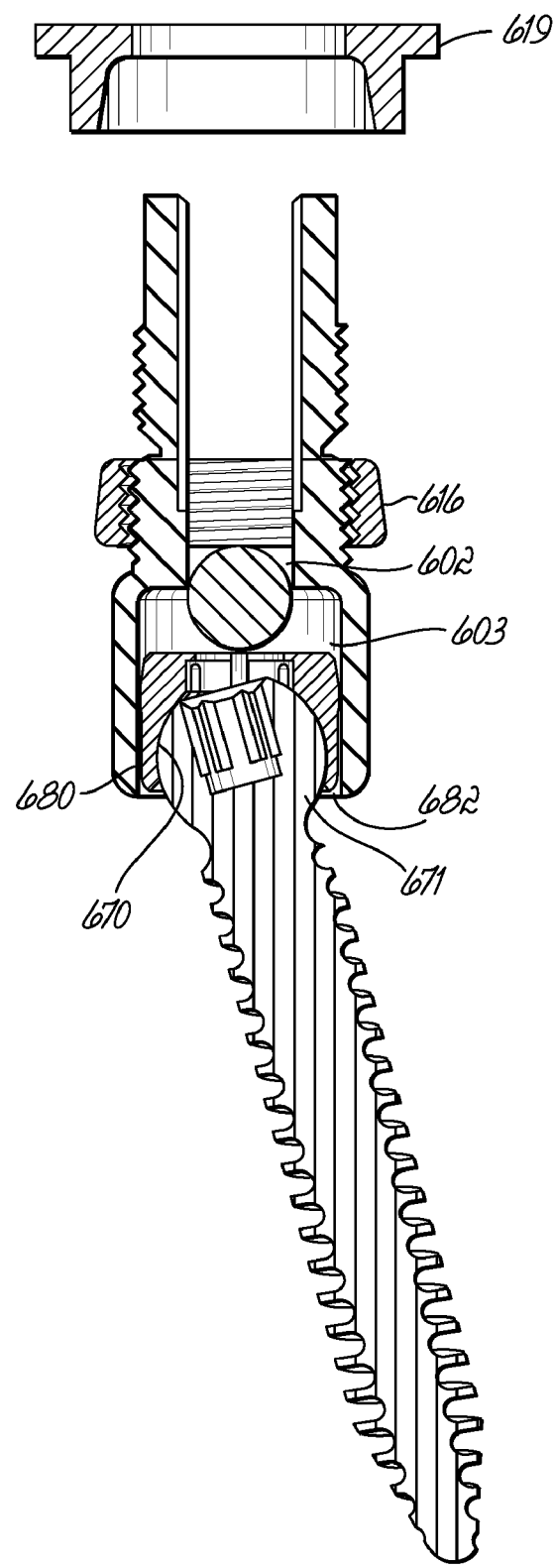
FIG. 27 is a cross-sectional view of the spinal fixation assembly of FIG. 25 showing the assembly in a non-finally clamped orientation.
Figure 28:
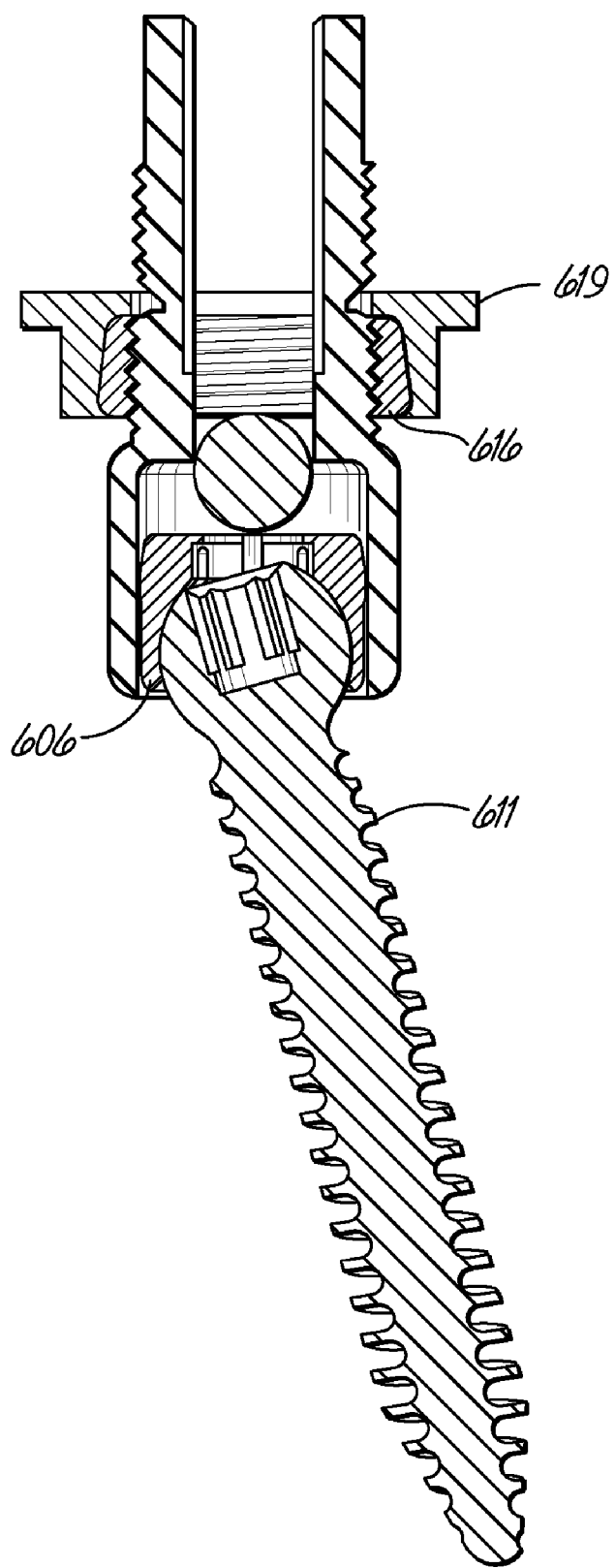
FIG. 28 is a cross-sectional view of the spinal fixation assembly of FIG. 25 showing the assembly in a finally clamped orientation.

The fastening arrangement also includes an expansion plug 519 (shown in FIG. 24) adapted to fit within the interior opening 517 of the split member 516. The expansion plug 519 includes an enlarged head 583 and a tapered expansion portion 582 that projects axially outwardly from the head 583. In one embodiment, the tapered expansion portion 582 can have a taper angle that generally matches the taper angle of the interior of the split member 516.

In use of the rod coupler 485', a spinal stabilization rod is inserted through the horizontal through-hole 501. To lock the rod in place relative to the main body 513 of the rod coupler 485', the split member 516 is loosely threaded within the fastener opening 502 until the bottom end 34 of the member 516 is pressed snugly against the rod within the through-hole 501 as shown in FIG. 22. For example, the split member 516 can be manually threaded or threaded with the assistance of a torque wrench inserted into the interior opening 517 of the split member 516. After loosely threading the split member 516 into the fastener opening 502, the assembly is locked in place by linearly inserting the expansion plug 519 into the interior of the split member 516 as shown in FIG. 21. When the plug 519 is inserted into the split member 516, the split member 516 expands radially outwardly. As the split member 516 expands radially outwardly, upper ramp surfaces 516R (shown in FIG. 22) defined by the threads of the split member 516 ride under lower ramp surfaces 502R (shown in FIG. 22) defined by the threads within the fastener opening 502 of the main body 513 causing the split member 516 to be driven linearly downwardly against the rod.

In this embodiment, the main body 513 is tension loaded and the member 516 is compression loaded in the final clamped orientation. Preferably, the split member 516 is biased linearly downwardly with sufficient force to lock the rod relative to the main body 513 of the rod coupler 485'. An installation tool can be used to apply a downward linear force to the plug 519 and to simultaneously apply a substantially equal and opposite force to the body 513 to prevent force from being transferred to the patient as the assembly is moved to the finally clamped orientation.

FIGS. 25-28 illustrate another embodiment of a fixation assembly 608 for use in stabilization of the vertebrae. The embodiment shown in FIGS. 25-28 has a polyaxial screw locking arrangement having features similar to embodiments disclosed in U.S. Pat. Nos. 5,863,293; 5,964,760; and 6,132,432, which are incorporated herein by reference in their entireties.

The embodiment of FIGS. 25-28 includes a receiver 613 having a rod receiving pocket 602 and an anchor receiving pocket 603. The rod receiving pocket 602 is defined between legs 605 of the receiver 613. The anchor receiving pocket 603 is adapted to house a retainer 606. A screw 611 is coupled to the retainer 606 within the pocket 603. The retainer 606 preferably includes a generally spherical cavity 670 that receives a generally spherical head 671 of the screw 611. The relative shapes of the head 671 and the cavity 670 allow the head 671 to pivot/rotate within the retainer 606 to allow the orientation of the axis of the screw 611 to be angularly adjusted relative to the receiver 613 prior to final fixation.

The assembly also includes a final fastening arrangement including a split ring 616 and a compression ring 619. The final fastening arrangement is adapted for locking the screw 611 at a final axial position relative to the receiver 613, and for locking a rod within the rod receiving pocket 602. The retainer 606 includes flexible legs 673 that define the cavity 670. When the retainer 606 is mounted in the anchor receiving pocket 603, a top end 677 of the retainer 606 is exposed the rod receiving pocket 602 of the receiver 613. The anchor receiving pocket 603 of the receiver 613 includes a tapered internal surface 680 defining a diameter that reduces in size as the surface 680 extends downwardly away from the rod receiving pocket 602. The anchor receiving pocket 603 includes a lower opening 682 through which the retainer 606 and the head of the screw 611 can be bottom loaded into the receiver 613. To bottom load the screw 611 into the receiver 613, the retainer 606 is first inserted into the anchor receiving pocket 603 through the lower opening 682. After the retainer 606 has been inserted into the anchor receiving pocket 603, the head of the screw 611 is inserted through the lower opening 682 and snapped into the cavity 670 of the retainer 606. When the head of the screw 611 is inserted into the cavity 670, the retainer 606 expands thereby preventing the retainer 606 and the screw head from being removed from the pocket 603 without using a removal tool.

In use, the screws and receiver assemblies are anchored to bones desired to be stabilized. Rods are then inserted into the rod receiving pockets 602 of the receivers 613 to interconnect the anchored assemblies and thereby form a rod/implant construct. The rods can be provisionally retained within the pockets 602 by manually threading the split rings 616 about the exterior of the receiver 613. With the split rings 616 provisionally mounted on the legs, the polyaxial positions of the screws 611 can be adjusted relative to their corresponding receivers 613 to make final adjustments to the rod/connector construct. The positioning of the rods can also be adjusted. Once the final adjustments have been made, the split rings 616 can be further manually threaded onto the legs until a pre-final locking position is reached in which the rings 616 are snug against the rods (see FIG. 27). Thereafter, the compression rings 619 is forced about the exteriors of the split rings 616 causing the spit rings to be forced radially inwardly (see FIG. 28). As the split rings 616 are compressed radially inwardly, ramp surfaces provided by internal threads of the split rings 616 slide relative to corresponding ramp surfaces provided by external threads on the legs 605 thereby axially tensioning the legs causing the split rings 616 to be forced against the top sides of the rods to finally lock the rods in place.

When forces are applied to the top sides of the rods, the rods also press downwardly on the retainers 606 to lock the angular position of the bone screws 611. In other embodiments, rather than directly engaging the top sides of the rods, radial compression of the split ring may cause the legs 605 to be flexed together to clamp the rod in place and also to force the rod slightly downwardly to compress the retainer into the locked position.

The embodiments disclosed herein are all depicted including anchors in the form of screws. It will be appreciated that other anchors such as pins, hooks, rivets or other structures could also be used.

The embodiments disclosed herein include various components such as receivers, anchors, sleeves, split rings, compression rings, connectors and other components. It will be appreciated that these components can be manufactured from different types of materials. A preferred material includes titanium. Other example material include nitinol, stainless steel, thermal plastic polymers, thermal set polymers as well as other materials.

As used herein, the term "connector" is used to define members of a construct used to interconnect bone anchors. Example connectors include rods, plates or other members.

From the forgoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

We claim:

1. A spinal fixation assembly comprising:
    a connector including a rod coupler and an extension plate that projects outwardly from the rod coupler, the extension plate defining a through-hole;
    a collar positioned at an underside of the extension plate;
    a bone screw including a head defining a socket, the head of the bone screw being mounted at least partially within an underside of the collar;
    a fastener including a head that mounts within the socket of the bone screw, and a shank that extends through the collar and the through-hole of the extension plate;
    a split ring that mounts on the threaded shank; and
    a compression ring that is linearly forced over the exterior of the split ring to compress the split ring relative to the shank;
    wherein the shank is externally threaded and the split ring is internally threaded.

2. The assembly of claim 1, wherein the split ring defines at least one slit that extends completely through the split ring.

3. The assembly of claim 1, wherein ramp structures are provided at an interface between the shank and the split ring.

* * * * *